(12) United States Patent
Inagaki et al.

(10) Patent No.: US 7,118,903 B2
(45) Date of Patent: Oct. 10, 2006

(54) L-METHIONINE $G(G)-LYASE WITH MODIFIED FUNCTION

(75) Inventors: Kenji Inagaki, Okayama (JP); Hidehiko Tanaka, Okayama (JP); Akio Takimoto, Amagasaki (JP); Tomoaki Takakura, Amagasaki (JP); Shintaro Misaki, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 432 days.

(21) Appl. No.: 10/362,924

(22) PCT Filed: Aug. 24, 2001

(86) PCT No.: PCT/JP01/07271

§ 371 (c)(1),
(2), (4) Date: Feb. 27, 2003

(87) PCT Pub. No.: WO02/20807

PCT Pub. Date: Mar. 14, 2002

(65) Prior Publication Data

US 2004/0110164 A1    Jun. 10, 2004

(30) Foreign Application Priority Data

Sep. 5, 2000    (JP) .............................. 2000-268314

(51) Int. Cl.
*C12N 9/88* (2006.01)
*C12Q 1/68* (2006.01)
*C12P 21/00* (2006.01)
*C07H 21/04* (2006.01)

(52) U.S. Cl. .................. 435/232; 435/6; 435/69.1; 435/320.1; 536/23.2

(58) Field of Classification Search ............. 435/6, 435/232; 530/300
See application file for complete search history.

(56) References Cited

U.S. PATENT DOCUMENTS 5,861,154 A    1/1999    Soda et al.

FOREIGN PATENT DOCUMENTS

JP    7-227282 A    8/1995

WO    WO 94/11535 A1    5/1994
WO    WO 96/40284 A1    12/1996

OTHER PUBLICATIONS

Inoue et al. Role of tyrosine 114 of L-methionine gamma lyase from *Pseudomonas putida*, Biosci. Biotechnol. Biochem. 64(11): 2336-2343, 2000.*
T. Nakayama et al., Analytical Biochemistry, 138, 421-424 (1984).
H. Tanaka et al., Biochemistry, vol. 16, No. 1, 1977, 100-107.
N. Esaki et al., FEBS Letters, vol. 84, No. 2, Dec. 1997, 309-312.
T. Nakayama et al., Biochemistry, 1988, 27, 1587-1591.
R. M. Hoffman, Human Cell, vol. 10, No. 1, 1997, 69-80.
T. Yoshioka et al., Cancer Research, 58, 2583-2587, Jun. 15, 1998.
B. Dias et al., Applied and Environmental Microbiology, vol. 64, No. 9, Sep. 1998, pp. 3327-3331.
H. Inoue et al., Biosci. Biotechnol. Biochem. 64(11), 2336-2343, 2000.
H. Motoshima et al., J. Biochem., 128, 349-354 (2000).
H. Hori et al., Cancer Research, 56, 2116-2122, May 1, 1996.
Y. Tan et al., Protein Expression and Purification, 9, 223-245 (1997).
Motoshima H. et al., J. Biochem, vol. 128, No. 3, pp. 349-354, (2000).
Inoue H. et al., J. Biochem, vol. 117, No. 5, pp. 1120-1125, (1995).
Tan Y. et al., Protein Expr. Purif, vol. 12, No. 1, pp. 45-52, (1995).
Esaki N. et al., Methods Enzymol, vol. 143, pp. 459-465, (1987).
Vermeij P. et al., J. Bacteriol, vol. 181, No. 18, pp. 5833-5837, (1999).
McKie A.E. et al., J. Biol. Chem., vol. 273, No. 10, pp. 5549-5556, (1998).

* cited by examiner

*Primary Examiner*—Rebecca E. Prouty
*Assistant Examiner*—Iqbal Chowdhury
(74) *Attorney, Agent, or Firm*—Birch, Stewart, Kolasch & Birch, LLP

(57) ABSTRACT

An L-methionine γ-lyase having modified function which is obtained by structurally stabilizing natural L-methionine γ-lyase by analyzing the structure of crystals thereof by using X-ray, estimating an amino acid sequence concerning its substrate specificity and varying amino acid residue thereof; enzymes comprising a protein constituting the L-methionine γ-lyase having modified function or its multimer (preferably its tetramer); DNA sequences encoding these enzymes; a process for producing these enzymes; and medicinal preparations (preferably anticancer agent) containing these enzymes.

14 Claims, 9 Drawing Sheets

SEQUENCE LISTING

<160> NUMBER OF SEQ ID NOS: 26

<210> SEQ ID NO 1
<211> LENGTH: 398
<212> TYPE: PRT
<213> ORGANISM: Pseudomonas putida
<300> PUBLICATION INFORMATION:
<301> AUTHORS: Inoue, Hiroyuki
<302> TITLE: Structural Analysis of the L-Methionine Gamma-Lyase Gene
       From Pseudomonas putida
<303> JOURNAL: Journal of Biological Chemistry
<304> VOLUME: 117
<305> ISSUE: 5
<306> PAGES: 1120-1125
<307> DATE: 1995-05-01
<313> RELEVANT RESIDUES: (1)..(398)

<400> SEQUENCE: 1

```
Met His Gly Ser Asn Lys Leu Pro Gly Phe Ala Thr Arg Ala Ile His
1               5                   10                  15

His Gly Tyr Asp Pro Gln Asp His Gly Gly Ala Leu Val Pro Pro Val
            20                  25                  30

Tyr Gln Thr Ala Thr Phe Thr Phe Pro Thr Val Glu Tyr Gly Ala Ala
        35                  40                  45

Cys Phe Ala Gly Glu Gln Ala Gly His Phe Tyr Ser Arg Ile Ser Asn
    50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
            100                 105                 110

Leu Tyr Gly Cys Thr Phe Ala Phe Leu His His Gly Ile Gly Glu Phe
        115                 120                 125

Gly Val Lys Leu Arg His Val Asp Met Ala Asp Leu Gln Ala Leu Glu
    130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Val Asp Asn Thr Tyr Cys Thr Pro
            180                 185                 190

Tyr Leu Gln Arg Pro Leu Glu Leu Gly Ala Asp Leu Val Val His Ser
        195                 200                 205

Ala Thr Lys Tyr Leu Ser Gly His Gly Asp Ile Thr Ala Gly Ile Val
    210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
            260                 265                 270

Ala Gln Val Leu Ala Glu Phe Leu Ala Arg Gln Pro Gln Val Glu Leu
        275                 280                 285

Ile His Tyr Pro Gly Leu Ala Ser Phe Pro Gln Tyr Thr Leu Ala Arg
    290                 295                 300
```

```
Gln Gln Met Ser Gln Pro Gly Met Ile Ala Phe Glu Leu Lys Gly
305                 310                 315                 320

Gly Ile Gly Ala Gly Arg Arg Phe Met Asn Ala Leu Gln Leu Phe Ser
            325                 330                 335

Arg Ala Val Ser Leu Gly Asp Ala Glu Ser Leu Ala Gln His Pro Ala
            340                 345                 350

Ser Met Thr His Ser Ser Tyr Thr Pro Glu Glu Arg Ala His Tyr Gly
            355                 360                 365

Ile Ser Glu Gly Leu Val Arg Leu Ser Val Gly Leu Glu Asp Ile Asp
            370                 375                 380

Asp Leu Leu Ala Asp Val Gln Gln Ala Leu Lys Ala Ser Ala
385                 390                 395
```

<210> SEQ ID NO 2
<211> LENGTH: 398
<212> TYPE: PRT
<213> ORGANISM: Artificial Sequence
<220> FEATURE:
<223> OTHER INFORMATION: G9C and D385C enzyme, variant of SEQ ID NO:1,
      directed to Human L-methionine Gamma-lyase
      gene.

<400> SEQUENCE: 2

```
Met His Gly Ser Asn Lys Leu Pro Cys Phe Ala Thr Arg Ala Ile His
1               5                   10                  15

His Gly Tyr Asp Pro Gln Asp His Gly Ala Leu Val Pro Pro Val
            20                  25                  30

Tyr Gln Thr Ala Thr Phe Thr Phe Pro Thr Val Glu Tyr Gly Ala Ala
            35                  40                  45

Cys Phe Ala Gly Glu Gln Ala Gly His Phe Tyr Ser Arg Ile Ser Asn
50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
            100                 105                 110

Leu Tyr Gly Cys Thr Phe Ala Phe Leu His His Gly Ile Gly Glu Phe
            115                 120                 125

Gly Val Lys Leu Arg His Val Asp Met Ala Asp Leu Gln Ala Leu Glu
130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Val Asp Asn Thr Tyr Cys Thr Pro
            180                 185                 190

Tyr Leu Gln Arg Pro Leu Glu Leu Gly Ala Asp Leu Val Val His Ser
            195                 200                 205

Ala Thr Lys Tyr Leu Ser Gly His Gly Asp Ile Thr Ala Gly Ile Val
            210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
```

```
                    260                 265                 270
Ala Gln Val Leu Ala Glu Phe Leu Ala Arg Gln Pro Gln Val Glu Leu
                275                 280                 285

Ile His Tyr Pro Gly Leu Ala Ser Phe Pro Gln Tyr Thr Leu Ala Arg
            290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
            340                 345                 350

Ser Met Thr His Ser Ser Tyr Thr Pro Glu Glu Arg Ala His Tyr Gly
                355                 360                 365

Ile Ser Glu Gly Leu Val Arg Leu Ser Val Gly Leu Glu Asp Ile Asp
            370                 375                 380

Cys Leu Leu Ala Asp Val Gln Gln Ala Leu Lys Ala Ser Ala
385                 390                 395

<210> SEQ ID NO 3
<211> LENGTH: 398
<212> TYPE: PRT
<213> ORGANISM: Artificial Sequence
<220> FEATURE:
<223> OTHER INFORMATION: K6H enzyme, variant of SEQ ID NO:1, directed to
                        Human L-methionine Gamma-lyase gene.

<400> SEQUENCE: 3

Met His Gly Ser Asn His Leu Pro Gly Phe Ala Thr Arg Ala Ile His
1               5                   10                  15

His Gly Tyr Asp Pro Gln Asp His Gly Gly Ala Leu Val Pro Pro Val
                20                  25                  30

Tyr Gln Thr Ala Thr Phe Thr Phe Pro Thr Val Glu Tyr Gly Ala Ala
            35                  40                  45

Cys Phe Ala Gly Glu Gln Ala Gly His Phe Tyr Ser Arg Ile Ser Asn
        50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
            100                 105                 110

Leu Tyr Gly Cys Thr Phe Ala Phe Leu His His Gly Ile Gly Glu Phe
        115                 120                 125

Gly Val Lys Leu Arg His Val Asp Met Ala Asp Leu Gln Ala Leu Glu
    130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Asp Asn Thr Tyr Cys Thr Pro
            180                 185                 190

Tyr Leu Gln Arg Pro Leu Glu Leu Gly Ala Asp Leu Val Val His Ser
        195                 200                 205

Ala Thr Lys Tyr Leu Ser Gly His Gly Asp Ile Thr Ala Gly Ile Val
    210                 215                 220
```

-continued

```
Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
            245                 250                 255

Arg Gly Ile Lys Thr Leu Asn Leu Arg Met Asp Arg His Cys Ala Asn
                260                 265                 270

Ala Gln Val Leu Ala Glu Phe Leu Ala Arg Gln Pro Gln Val Glu Leu
            275                 280                 285

Ile His Tyr Pro Gly Leu Ala Ser Phe Pro Gln Tyr Thr Leu Ala Arg
        290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
            340                 345                 350

Ser Met Thr His Ser Ser Tyr Thr Pro Glu Glu Arg Ala His Tyr Gly
        355                 360                 365

Ile Ser Glu Gly Leu Val Arg Leu Ser Val Gly Leu Glu Asp Ile Asp
        370                 375                 380

Asp Leu Leu Ala Asp Val Gln Gln Ala Leu Lys Ala Ser Ala
385                 390                 395
```

<210> SEQ ID NO 4

<400> SEQUENCE: 4

000

<210> SEQ ID NO 5
<211> LENGTH: 398
<212> TYPE: PRT
<213> ORGANISM: Artificial Sequence
<220> FEATURE:
<223> OTHER INFORMATION: L7P enzyme, variant of SEQ ID NO:1, directed to
               Human L-methionine Gamma-lyase gene.

<400> SEQUENCE: 5

```
Met His Gly Ser Asn Lys Pro Gly Phe Ala Thr Arg Ala Ile His
1               5                   10                  15

His Gly Tyr Asp Pro Gln Asp His Gly Gly Ala Leu Val Pro Pro Val
            20                  25                  30

Tyr Gln Thr Ala Thr Phe Thr Phe Pro Thr Val Glu Tyr Gly Ala Ala
        35                  40                  45

Cys Phe Ala Gly Glu Gln Ala Gly His Phe Tyr Ser Arg Ile Ser Asn
    50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
                100                 105                 110

Leu Tyr Gly Cys Thr Phe Ala Phe Leu His His Gly Ile Gly Glu Phe
            115                 120                 125

Gly Val Lys Leu Arg His Val Asp Met Ala Asp Leu Gln Ala Leu Glu
        130                 135                 140

Ala Ala Met Thr Pro Ala Thr Arg Val Ile Tyr Phe Glu Ser Pro Ala
```

```
                145                 150                 155                 160
Asn Pro Asn Met His Met Ala Asp Ile Ala Gly Val Ala Lys Ile Ala
                    165                 170                 175
Arg Lys His Gly Ala Thr Val Val Asp Asn Thr Tyr Cys Thr Pro
                180                 185                 190
Tyr Leu Gln Arg Pro Leu Glu Leu Gly Ala Asp Leu Val His Ser
            195                 200                 205
Ala Thr Lys Tyr Leu Ser Gly His Gly Asp Ile Thr Ala Gly Ile Val
        210                 215                 220
Val Gly Ser Gln Ala Leu Val Asp Arg Ile Arg Leu Gln Gly Leu Lys
225                 230                 235                 240
Asp Met Thr Gly Ala Val Leu Ser Pro His Asp Ala Ala Leu Leu Met
                245                 250                 255
Arg Gly Ile Lys Thr Leu Asn Leu Arg Met Asp Arg His Cys Ala Asn
                260                 265                 270
Ala Gln Val Leu Ala Glu Phe Leu Ala Arg Gln Pro Gln Val Glu Leu
            275                 280                 285
Ile His Tyr Pro Gly Leu Ala Ser Phe Pro Gln Tyr Thr Leu Ala Arg
    290                 295                 300
Gln Gln Met Ser Gln Pro Gly Gly Met Ile Ala Phe Glu Leu Lys Gly
305                 310                 315                 320
Gly Ile Gly Ala Gly Arg Arg Phe Met Asn Ala Leu Gln Leu Phe Ser
                325                 330                 335
Arg Ala Val Ser Leu Gly Asp Ala Glu Ser Leu Ala Gln His Pro Ala
                340                 345                 350
Ser Met Thr His Ser Ser Tyr Thr Pro Glu Glu Arg Ala His Tyr Gly
                355                 360                 365
Ile Ser Glu Gly Leu Val Arg Leu Ser Val Gly Leu Glu Asp Ile Asp
    370                 375                 380
Asp Leu Leu Ala Asp Val Gln Gln Ala Leu Lys Ala Ser Ala
385                 390                 395

<210> SEQ ID NO 6
<211> LENGTH: 398
<212> TYPE: PRT
<213> ORGANISM: Artificial Sequence
<220> FEATURE:
<223> OTHER INFORMATION: K395H enzyme, variant of SEQ ID NO:1, directed
                        to Human L-methionine Gamma-lyase gene.

<400> SEQUENCE: 6

Met His Gly Ser Asn Lys Leu Pro Gly Phe Ala Thr Arg Ala Ile His
1               5                   10                  15
His Gly Tyr Asp Pro Gln Asp His Gly Gly Ala Leu Val Pro Pro Val
                20                  25                  30
Tyr Gln Thr Ala Thr Phe Thr Phe Pro Thr Val Glu Tyr Gly Ala Ala
            35                  40                  45
Cys Phe Ala Gly Glu Gln Ala Gly His Phe Tyr Ser Arg Ile Ser Asn
        50                  55                  60
Pro Thr Leu Asn Leu Leu Glu Ala Arg Met Ala Ser Leu Glu Gly Gly
65                  70                  75                  80
Glu Ala Gly Leu Ala Leu Ala Ser Gly Met Gly Ala Ile Thr Ser Thr
                85                  90                  95
Leu Trp Thr Leu Leu Arg Pro Gly Asp Glu Val Leu Leu Gly Asn Thr
                100                 105                 110
```

```
Leu Tyr Gly Cys Thr Phe Ala Phe Leu His His Gly Ile Gly Glu Phe
        115                 120                 125
Gly Val Lys Leu Arg His Val Asp Met Ala Asp Leu Gln Ala Leu Glu
    130                 135                 140
Ala Ala Met Thr Pro Ala Thr Arg Val Ile Tyr Phe Glu Ser Pro Ala
145                 150                 155                 160
Asn Pro Asn Met His Met Ala Asp Ile Ala Gly Val Ala Lys Ile Ala
                165                 170                 175
Arg Lys His Gly Ala Thr Val Val Asp Asn Thr Tyr Cys Thr Pro
            180                 185                 190
Tyr Leu Gln Arg Pro Leu Glu Leu Gly Ala Asp Leu Val His Ser
        195                 200                 205
Ala Thr Lys Tyr Leu Ser Gly His Gly Asp Ile Thr Ala Gly Ile Val
    210                 215                 220
Val Gly Ser Gln Ala Leu Val Asp Arg Ile Arg Leu Gln Gly Leu Lys
225                 230                 235                 240
Asp Met Thr Gly Ala Val Leu Ser Pro His Asp Ala Ala Leu Leu Met
                245                 250                 255
Arg Gly Ile Lys Thr Leu Asn Leu Arg Met Asp Arg His Cys Ala Asn
            260                 265                 270
Ala Gln Val Leu Ala Glu Phe Leu Ala Arg Gln Pro Gln Val Glu Leu
        275                 280                 285
Ile His Tyr Pro Gly Leu Ala Ser Phe Pro Gln Tyr Thr Leu Ala Arg
    290                 295                 300
Gln Gln Met Ser Gln Pro Gly Gly Met Ile Ala Phe Glu Leu Lys Gly
305                 310                 315                 320
Gly Ile Gly Ala Gly Arg Arg Phe Met Asn Ala Leu Gln Leu Phe Ser
                325                 330                 335
Arg Ala Val Ser Leu Gly Asp Ala Glu Ser Leu Ala Gln His Pro Ala
            340                 345                 350
Ser Met Thr His Ser Ser Tyr Thr Pro Glu Glu Arg Ala His Tyr Gly
        355                 360                 365
Ile Ser Glu Gly Leu Val Arg Leu Ser Val Gly Leu Glu Asp Ile Asp
    370                 375                 380
Asp Leu Leu Ala Asp Val Gln Gln Ala Leu His Ala Ser Ala
385                 390                 395

<210> SEQ ID NO 7

<400> SEQUENCE: 7

000

<210> SEQ ID NO 8
<211> LENGTH: 398
<212> TYPE: PRT
<213> ORGANISM: Artificial Sequence
<220> FEATURE:
<223> OTHER INFORMATION: A396P enzyme, variant of SEQ ID NO:1, directed
                         to Human L-methionine Gamma-lyase gene.

<400> SEQUENCE: 8

Met His Gly Ser Asn Lys Leu Pro Gly Phe Ala Thr Arg Ala Ile His
1               5                   10                  15
His Gly Tyr Asp Pro Gln Asp His Gly Gly Ala Leu Val Pro Pro Val
            20                  25                  30
Tyr Gln Thr Ala Thr Phe Thr Phe Pro Thr Val Glu Tyr Gly Ala Ala
```

```
                35                  40                  45
Cys Phe Ala Gly Glu Gln Ala Gly His Phe Tyr Ser Arg Ile Ser Asn
 50                  55                  60

Pro Thr Leu Asn Leu Leu Glu Ala Arg Met Ala Ser Leu Glu Gly Gly
 65                  70                  75                  80

Glu Ala Gly Leu Ala Leu Ala Ser Gly Met Gly Ala Ile Thr Ser Thr
                 85                  90                  95

Leu Trp Thr Leu Leu Arg Pro Gly Asp Glu Val Leu Leu Gly Asn Thr
                100                 105                 110

Leu Tyr Gly Cys Thr Phe Ala Phe Leu His His Gly Ile Gly Glu Phe
            115                 120                 125

Gly Val Lys Leu Arg His Val Asp Met Ala Asp Leu Gln Ala Leu Glu
130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Asp Asn Thr Tyr Cys Thr Pro
            180                 185                 190        Pro

Tyr Leu Gln Arg Pro Leu Glu Leu Gly Ala Asp Leu Val Val His Ser
            195                 200                 205

Ala Thr Lys Tyr Leu Ser Gly His Gly Asp Ile Thr Ala Gly Ile Val
            210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
                260                 265                 270

Ala Gln Val Leu Ala Glu Phe Leu Ala Arg Gln Pro Gln Val Glu Leu
            275                 280                 285

Ile His Tyr Pro Gly Leu Ala Ser Phe Pro Gln Tyr Thr Leu Ala Arg
290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
            340                 345                 350

Ser Met Thr His Ser Ser Tyr Thr Pro Glu Glu Arg Ala His Tyr Gly
            355                 360                 365

Ile Ser Glu Gly Leu Val Arg Leu Ser Val Gly Leu Glu Asp Ile Asp
370                 375                 380

Asp Leu Leu Ala Asp Val Gln Gln Ala Leu Lys Pro Ser Ala
385                 390                 395

<210> SEQ ID NO 9
<211> LENGTH: 398
<212> TYPE: PRT
<213> ORGANISM: Artificial Sequence
<220> FEATURE:
<223> OTHER INFORMATION: F128C enzyme, variant of SEQ ID NO:1, directed
                         to Human L-methionine Gamma-lyase gene.

<400> SEQUENCE: 9
```

```
Met His Gly Ser Asn Lys Leu Pro Gly Phe Ala Thr Arg Ala Ile His
1               5                   10                  15

His Gly Tyr Asp Pro Gln Asp His Gly Ala Leu Val Pro Pro Val
            20              25                  30

Tyr Gln Thr Ala Thr Phe Thr Phe Pro Thr Val Glu Tyr Gly Ala Ala
            35              40                  45

Cys Phe Ala Gly Glu Gln Ala Gly His Phe Tyr Ser Arg Ile Ser Asn
50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
                100                 105                 110

Leu Tyr Gly Cys Thr Phe Ala Phe Leu His His Gly Ile Gly Glu Cys
            115                 120                 125

Gly Val Lys Leu Arg His Val Asp Met Ala Asp Leu Gln Ala Leu Glu
            130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Asp Asn Thr Tyr Cys Thr Pro
            180                 185                 190

Tyr Leu Gln Arg Pro Leu Glu Leu Gly Ala Asp Leu Val Val His Ser
            195                 200                 205

Ala Thr Lys Tyr Leu Ser Gly His Gly Asp Ile Thr Ala Gly Ile Val
210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
                260                 265                 270

Ala Gln Val Leu Ala Glu Phe Leu Ala Arg Gln Pro Gln Val Glu Leu
            275                 280                 285

Ile His Tyr Pro Gly Leu Ala Ser Phe Pro Gln Tyr Thr Leu Ala Arg
290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
            340                 345                 350

Ser Met Thr His Ser Ser Tyr Thr Pro Glu Glu Arg Ala His Tyr Gly
            355                 360                 365

Ile Ser Glu Gly Leu Val Arg Leu Ser Val Gly Leu Glu Asp Ile Asp
            370                 375                 380

Asp Leu Leu Ala Asp Val Gln Gln Ala Leu Lys Ala Ser Ala
385                 390                 395
```

<210> SEQ ID NO 10
<211> LENGTH: 398
<212> TYPE: PRT

<213> ORGANISM: Artificial Sequence
<220> FEATURE:
<223> OTHER INFORMATION: S248C enzyme, variant of SEQ ID NO:1, directed
to Human L-methionine Gamma-lyase gene.

<400> SEQUENCE: 10

```
Met His Gly Ser Asn Lys Leu Pro Gly Phe Ala Thr Arg Ala Ile His
1               5                   10                  15

His Gly Tyr Asp Pro Gln Asp His Gly Ala Leu Val Pro Pro Val
            20                  25                  30

Tyr Gln Thr Ala Thr Phe Thr Phe Pro Thr Val Glu Tyr Gly Ala Ala
            35                  40                  45

Cys Phe Ala Gly Glu Gln Ala Gly His Phe Tyr Ser Arg Ile Ser Asn
50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
            100                 105                 110

Leu Tyr Gly Cys Thr Phe Ala Phe Leu His His Gly Ile Gly Glu Phe
            115                 120                 125

Gly Val Lys Leu Arg His Val Asp Met Ala Asp Leu Gln Ala Leu Glu
130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Asp Asn Thr Tyr Cys Thr Pro
            180                 185                 190

Tyr Leu Gln Arg Pro Leu Glu Leu Gly Ala Asp Leu Val Val His Ser
            195                 200                 205

Ala Thr Lys Tyr Leu Ser Gly His Gly Asp Ile Thr Ala Gly Ile Val
210                 215                 220

Val Gly Ser Gln Ala Leu Val Asp Arg Ile Arg Leu Gln Gly Leu Lys
225                 230                 235                 240

Asp Met Thr Gly Ala Val Leu Cys Pro His Asp Ala Ala Leu Leu Met
                245                 250                 255

Arg Gly Ile Lys Thr Leu Asn Leu Arg Met Asp Arg His Cys Ala Asn
            260                 265                 270

Ala Gln Val Leu Ala Glu Phe Leu Ala Arg Gln Pro Gln Val Glu Leu
            275                 280                 285

Ile His Tyr Pro Gly Leu Ala Ser Phe Pro Gln Tyr Thr Leu Ala Arg
290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
            340                 345                 350

Ser Met Thr His Ser Ser Tyr Thr Pro Glu Glu Arg Ala His Tyr Gly
            355                 360                 365

Ile Ser Glu Gly Leu Val Arg Leu Ser Val Gly Leu Glu Asp Ile Asp
370                 375                 380
```

Asp Leu Leu Ala Asp Val Gln Gln Ala Leu Lys Ala Ser Ala
385                 390                 395

<210> SEQ ID NO 11
<211> LENGTH: 398
<212> TYPE: PRT
<213> ORGANISM: Artificial Sequence
<220> FEATURE:
<223> OTHER INFORMATION: C116D enzyme, variant of SEQ ID NO:1, directed
      to Human L-methionine Gamma-lyase gene.

<400> SEQUENCE: 11

Met His Gly Ser Asn Lys Leu Pro Gly Phe Ala Thr Arg Ala Ile His
1               5                   10                  15

His Gly Tyr Asp Pro Gln Asp His Gly Ala Leu Val Pro Pro Val
            20                  25                  30

Tyr Gln Thr Ala Thr Phe Thr Phe Pro Thr Val Glu Tyr Gly Ala Ala
            35                  40                  45

Cys Phe Ala Gly Glu Gln Ala Gly His Phe Tyr Ser Arg Ile Ser Asn
    50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
            100                 105                 110

Leu Tyr Gly Asp Thr Phe Ala Phe Leu His His Gly Ile Gly Glu Phe
        115                 120                 125

Gly Val Lys Leu Arg His Val Asp Met Ala Asp Leu Gln Ala Leu Glu
130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Val Asp Asn Thr Tyr Cys Thr Pro
            180                 185                 190

Tyr Leu Gln Arg Pro Leu Glu Leu Gly Ala Asp Leu Val Val His Ser
        195                 200                 205

Ala Thr Lys Tyr Leu Ser Gly His Gly Asp Ile Thr Ala Gly Ile Val
210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
            260                 265                 270

Ala Gln Val Leu Ala Glu Phe Leu Ala Arg Gln Pro Gln Val Glu Leu
        275                 280                 285

Ile His Tyr Pro Gly Leu Ala Ser Phe Pro Gln Tyr Thr Leu Ala Arg
290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
            340                 345                 350

```
Ser Met Thr His Ser Ser Tyr Thr Pro Glu Glu Arg Ala His Tyr Gly
        355                 360                 365

Ile Ser Glu Gly Leu Val Arg Leu Ser Val Gly Leu Glu Asp Ile Asp
    370                 375                 380

Asp Leu Leu Ala Asp Val Gln Gln Ala Leu Lys Ala Ser Ala
385                 390                 395

<210> SEQ ID NO 12
<211> LENGTH: 398
<212> TYPE: PRT
<213> ORGANISM: Artificial Sequence
<220> FEATURE:
<223> OTHER INFORMATION: A119S enzyme, variant of SEQ ID NO:1, directed
                        to Human L-methionine Gamma-lyase gene.

<400> SEQUENCE: 12

Met His Gly Ser Asn Lys Leu Pro Gly Phe Ala Thr Arg Ala Ile His
1               5                   10                  15

His Gly Tyr Asp Pro Gln Asp His Gly Gly Ala Leu Val Pro Pro Val
            20                  25                  30

Tyr Gln Thr Ala Thr Phe Thr Phe Pro Thr Val Glu Tyr Gly Ala Ala
        35                  40                  45

Cys Phe Ala Gly Glu Gln Ala Gly His Phe Tyr Ser Arg Ile Ser Asn
50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
            100                 105                 110

Leu Tyr Gly Cys Thr Phe Ser Phe Leu His His Gly Ile Gly Glu Phe
        115                 120                 125

Gly Val Lys Leu Arg His Val Asp Met Ala Asp Leu Gln Ala Leu Glu
130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Asp Asn Thr Tyr Cys Thr Pro
        180                 185                 190

Tyr Leu Gln Arg Pro Leu Glu Leu Gly Ala Asp Leu Val Val His Ser
        195                 200                 205

Ala Thr Lys Tyr Leu Ser Gly His Gly Asp Ile Thr Ala Gly Ile Val
    210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
            260                 265                 270

Ala Gln Val Leu Ala Glu Phe Leu Ala Arg Gln Pro Gln Val Glu Leu
        275                 280                 285

Ile His Tyr Pro Gly Leu Ala Ser Phe Pro Gln Tyr Thr Leu Ala Arg
    290                 295                 300

Gln Gln Met Ser Gln Pro Gly Gly Met Ile Ala Phe Glu Leu Lys Gly
```

-continued

```
            305                 310                 315                 320
Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
                340                 345                 350

Ser Met Thr His Ser Ser Tyr Thr Pro Glu Glu Arg Ala His Tyr Gly
                355                 360                 365

Ile Ser Glu Gly Leu Val Arg Leu Ser Val Gly Leu Glu Asp Ile Asp
        370                 375                 380

Asp Leu Leu Ala Asp Val Gln Gln Ala Leu Lys Ala Ser Ala
385                 390                 395
```

<210> SEQ ID NO 13
<211> LENGTH: 398
<212> TYPE: PRT
<213> ORGANISM: Artificial Sequence
<220> FEATURE:
<223> OTHER INFORMATION: R61K enzyme, variant of SEQ ID NO:1, directed to Human L-methionine Gamma-lyase gene.

<400> SEQUENCE: 13

```
Met His Gly Ser Asn Lys Leu Pro Gly Phe Ala Thr Arg Ala Ile His
1               5                   10                  15

His Gly Tyr Asp Pro Gln Asp His Gly Gly Ala Leu Val Pro Pro Val
                20                  25                  30

Tyr Gln Thr Ala Thr Phe Thr Phe Pro Thr Val Glu Tyr Gly Ala Ala
            35                  40                  45

Cys Phe Ala Gly Glu Gln Ala Gly His Phe Tyr Ser Lys Ile Ser Asn
        50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
            100                 105                 110

Leu Tyr Gly Cys Thr Phe Ala Phe Leu His His Gly Ile Gly Glu Phe
        115                 120                 125

Gly Val Lys Leu Arg His Val Asp Met Ala Asp Leu Gln Ala Leu Glu
    130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Asp Asn Thr Tyr Cys Thr Pro
            180                 185                 190

Tyr Leu Gln Arg Pro Leu Glu Leu Gly Ala Asp Leu Val Val His Ser
        195                 200                 205

Ala Thr Lys Tyr Leu Ser Gly His Gly Asp Ile Thr Ala Gly Ile Val
    210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
            260                 265                 270
```

```
Ala Gln Val Leu Ala Glu Phe Leu Ala Arg Gln Pro Gln Val Glu Leu
            275                 280                 285

Ile His Tyr Pro Gly Leu Ala Ser Phe Pro Gln Tyr Thr Leu Ala Arg
            290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
            325                 330                 335

Arg Ala Val Ser Leu Gly Asp Ala Glu Ser Leu Ala Gln His Pro Ala
            340                 345                 350

Ser Met Thr His Ser Ser Tyr Thr Pro Glu Glu Arg Ala His Tyr Gly
            355                 360                 365

Ile Ser Glu Gly Leu Val Arg Leu Ser Val Gly Leu Glu Asp Ile Asp
            370                 375                 380

Asp Leu Leu Ala Asp Val Gln Gln Ala Leu Lys Ala Ser Ala
385                 390                 395

<210> SEQ ID NO 14
<211> LENGTH: 398
<212> TYPE: PRT
<213> ORGANISM: Artificial Sequence
<220> FEATURE:
<223> OTHER INFORMATION: L341H enzyme, variant of SEQ ID NO:1, directed
                        to Human L-methionine Gamma-lyase gene.

<400> SEQUENCE: 14

Met His Gly Ser Asn Lys Leu Pro Gly Phe Ala Thr Arg Ala Ile His
1               5                   10                  15

His Gly Tyr Asp Pro Gln Asp His Gly Gly Ala Leu Val Pro Pro Val
            20                  25                  30

Tyr Gln Thr Ala Thr Phe Thr Phe Pro Thr Val Glu Tyr Gly Ala Ala
            35                  40                  45

Cys Phe Ala Gly Glu Gln Ala Gly His Phe Tyr Ser Arg Ile Ser Asn
    50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
            85                  90                  95

Leu Trp Thr Leu Leu Arg Pro Gly Asp Glu Val Leu Leu Gly Asn Thr
            100                 105                 110

Leu Tyr Gly Cys Thr Phe Ala Phe Leu His His Gly Ile Gly Glu Phe
        115                 120                 125

Gly Val Lys Leu Arg His Val Asp Met Ala Asp Leu Gln Ala Leu Glu
    130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
            165                 170                 175

Arg Lys His Gly Ala Thr Val Val Val Asp Asn Thr Tyr Cys Thr Pro
            180                 185                 190

Tyr Leu Gln Arg Pro Leu Glu Leu Gly Ala Asp Leu Val Val His Ser
        195                 200                 205

Ala Thr Lys Tyr Leu Ser Gly His Gly Asp Ile Thr Ala Gly Ile Val
    210                 215                 220

Val Gly Ser Gln Ala Leu Val Asp Arg Ile Arg Leu Gln Gly Leu Lys
225                 230                 235                 240
```

```
Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
            260                 265                 270

Ala Gln Val Leu Ala Glu Phe Leu Ala Arg Gln Pro Gln Val Glu Leu
        275                 280                 285

Ile His Tyr Pro Gly Leu Ala Ser Phe Pro Gln Tyr Thr Leu Ala Arg
    290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser His Gly Asp Ala Glu Ser Leu Ala Gln His Pro Ala
            340                 345                 350

Ser Met Thr His Ser Ser Tyr Thr Pro Glu Glu Arg Ala His Tyr Gly
        355                 360                 365

Ile Ser Glu Gly Leu Val Arg Leu Ser Val Gly Leu Glu Asp Ile Asp
    370                 375                 380

Asp Leu Leu Ala Asp Val Gln Gln Ala Leu Lys Ala Ser Ala
385                 390                 395
```

```
<210> SEQ ID NO 15
<211> LENGTH: 39
<212> TYPE: DNA
<213> ORGANISM: Artificial Sequence
<220> FEATURE:
<223> OTHER INFORMATION: K6H, transformant of E. coli, JM109 strain.

<400> SEQUENCE: 15
ctatatgcac ggctccaacc atctcccagg atttgccac                         39

<210> SEQ ID NO 16
<211> LENGTH: 30
<212> TYPE: DNA
<213> ORGANISM: Artificial Sequence
<220> FEATURE:
<223> OTHER INFORMATION: C49S, transformant of E. coli, JM109 strain.

<400> SEQUENCE: 16
gaatacggcg ctgcgagctt tgccggcgag                                    30

<210> SEQ ID NO 17
<211> LENGTH: 27
<212> TYPE: DNA
<213> ORGANISM: Artificial Sequence
<220> FEATURE:
<223> OTHER INFORMATION: F128C, transformant of E. coli, JM109 strain.

<400> SEQUENCE: 17
ggcatcggcg agtgcggggt caagctg                                       27

<210> SEQ ID NO 18
<211> LENGTH: 30
<212> TYPE: DNA
<213> ORGANISM: Artificial Sequence
<220> FEATURE:
<223> OTHER INFORMATION: C190S, transformant of E. coli, JM109 strain.

<400> SEQUENCE: 18
gtcgacaaca cctacagcac gccgtacctg                                    30
```

<210> SEQ ID NO 19
<211> LENGTH: 27
<212> TYPE: DNA
<213> ORGANISM: Artificial Sequence
<220> FEATURE:
<223> OTHER INFORMATION: G217S, transformant of E. coli, JM109 strain.

<400> SEQUENCE: 19
cctgagcggc catagcgaca tcactgc                                    27

<210> SEQ ID NO 20
<211> LENGTH: 29
<212> TYPE: DNA
<213> ORGANISM: Artificial Sequence
<220> FEATURE:
<223> OTHER INFORMATION: S248C, transformant of E. coli, JM109 strain.

<400> SEQUENCE: 20
cggtgcggtg ctctgccccc atgacgccg                                  29

<210> SEQ ID NO 21
<211> LENGTH: 27
<212> TYPE: DNA
<213> ORGANISM: Artificial Sequence
<220> FEATURE:
<223> OTHER INFORMATION: L341H, transformant of E. coli, JM109 strain.

<400> SEQUENCE: 21
cgcgcggtga gccatggcga tgccgag                                    27

<210> SEQ ID NO 22
<211> LENGTH: 33
<212> TYPE: DNA
<213> ORGANISM: Artificial Sequence
<220> FEATURE:
<223> OTHER INFORMATION: D385C, transformant of E. coli, JM109 strain.

<400> SEQUENCE: 22
ctggaagaca tcgactgcct gctggccgat gtg                             33

<210> SEQ ID NO 23
<211> LENGTH: 30
<212> TYPE: DNA
<213> ORGANISM: Artificial Sequence
<220> FEATURE:
<223> OTHER INFORMATION: G9C, transformant of E. coli, JM109 strain.

<400> SEQUENCE: 23
ccaacaagct cccatgcttt gccacccgcg                                 30

<210> SEQ ID NO 24
<211> LENGTH: 398
<212> TYPE: PRT
<213> ORGANISM: Artificial Sequence
<220> FEATURE:
<223> OTHER INFORMATION: C49S enzyme, variant of SEQ ID NO:1, directed
                        to Human L-methionine Gamma-lyase gene.

<400> SEQUENCE: 24

Met His Gly Ser Asn Lys Leu Pro Gly Phe Ala Thr Arg Ala Ile His
1               5                   10                  15

His Gly Tyr Asp Pro Gln Asp His Gly Gly Ala Leu Val Pro Pro Val
            20                  25                  30

Tyr Gln Thr Ala Thr Phe Thr Phe Pro Thr Val Glu Tyr Gly Ala Ala
        35                  40                  45

```
Ser Phe Ala Gly Glu Gln Ala Gly His Phe Tyr Ser Arg Ile Ser Asn
 50                  55                  60

Pro Thr Leu Asn Leu Leu Glu Ala Arg Met Ala Ser Leu Glu Gly Gly
 65                  70                  75                  80

Glu Ala Gly Leu Ala Leu Ala Ser Gly Met Gly Ala Ile Thr Ser Thr
                 85                  90                  95

Leu Trp Thr Leu Arg Pro Gly Asp Glu Val Leu Leu Gly Asn Thr
                100                 105                 110

Leu Tyr Gly Cys Thr Phe Ala Phe Leu His His Gly Ile Gly Glu Phe
                115                 120                 125

Gly Val Lys Leu Arg His Val Asp Met Ala Asp Leu Gln Ala Leu Glu
130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Asp Asn Thr Tyr Cys Thr Pro
                180                 185                 190

Tyr Leu Gln Arg Pro Leu Glu Leu Gly Ala Asp Leu Val Val His Ser
                195                 200                 205

Ala Thr Lys Tyr Leu Ser Gly His Gly Asp Ile Thr Ala Gly Ile Val
210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
                260                 265                 270

Ala Gln Val Leu Ala Glu Phe Leu Ala Arg Gln Pro Gln Val Glu Leu
                275                 280                 285

Ile His Tyr Pro Gly Leu Ala Ser Phe Pro Gln Tyr Thr Leu Ala Arg
290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
                340                 345                 350

Ser Met Thr His Ser Ser Tyr Thr Pro Glu Glu Arg Ala His Tyr Gly
                355                 360                 365

Ile Ser Glu Gly Leu Val Arg Leu Ser Val Gly Leu Glu Asp Ile Asp
370                 375                 380

Asp Leu Leu Ala Asp Val Gln Gln Ala Leu Lys Ala Ser Ala
385                 390                 395

<210> SEQ ID NO 25
<211> LENGTH: 398
<212> TYPE: PRT
<213> ORGANISM: Artificial Sequence
<220> FEATURE:
<223> OTHER INFORMATION: C190S enzyme, variant of SEQ ID NO:1, directed
                        to Human L-methionine Gamma-lyase gene.

<400> SEQUENCE: 25

Met His Gly Ser Asn Lys Leu Pro Gly Phe Ala Thr Arg Ala Ile His
```

```
  1               5                  10                 15
His Gly Tyr Asp Pro Gln Asp His Gly Gly Ala Leu Val Pro Pro Val
             20                 25                 30

Tyr Gln Thr Ala Thr Phe Thr Phe Pro Thr Val Glu Tyr Gly Ala Ala
             35                 40                 45

Cys Phe Ala Gly Glu Gln Ala Gly His Phe Tyr Ser Arg Ile Ser Asn
 50                 55                 60

Pro Thr Leu Asn Leu Leu Glu Ala Arg Met Ala Ser Leu Glu Gly Gly
 65                 70                 75                 80

Glu Ala Gly Leu Ala Leu Ala Ser Gly Met Gly Ala Ile Thr Ser Thr
             85                 90                 95

Leu Trp Thr Leu Leu Arg Pro Gly Asp Glu Val Leu Leu Gly Asn Thr
            100                105                110

Leu Tyr Gly Cys Thr Phe Ala Phe Leu His His Gly Ile Gly Glu Phe
            115                120                125

Gly Val Lys Leu Arg His Val Asp Met Ala Asp Gln Ala Leu Glu
130                135                140

Ala Ala Met Thr Pro Ala Thr Arg Val Ile Tyr Phe Glu Ser Pro Ala
145                150                155                160

Asn Pro Asn Met His Met Ala Asp Ile Ala Gly Val Ala Lys Ile Ala
            165                170                175

Arg Lys His Gly Ala Thr Val Val Asp Asn Thr Tyr Ser Thr Pro
            180                185                190

Tyr Leu Gln Arg Pro Leu Glu Leu Gly Ala Asp Leu Val Val His Ser
            195                200                205

Ala Thr Lys Tyr Leu Ser Gly His Gly Asp Ile Thr Ala Gly Ile Val
210                215                220

Val Gly Ser Gln Ala Leu Val Asp Arg Ile Arg Leu Gln Gly Leu Lys
225                230                235                240

Asp Met Thr Gly Ala Val Leu Ser Pro His Asp Ala Ala Leu Leu Met
            245                250                255

Arg Gly Ile Lys Thr Leu Asn Leu Arg Met Asp Arg His Cys Ala Asn
            260                265                270

Ala Gln Val Leu Ala Glu Phe Leu Ala Arg Gln Pro Gln Val Glu Leu
            275                280                285

Ile His Tyr Pro Gly Leu Ala Ser Phe Pro Gln Tyr Thr Leu Ala Arg
            290                295                300

Gln Gln Met Ser Gln Pro Gly Gly Met Ile Ala Phe Glu Leu Lys Gly
305                310                315                320

Gly Ile Gly Ala Gly Arg Arg Phe Met Asn Ala Leu Gln Leu Phe Ser
            325                330                335

Arg Ala Val Ser Leu Gly Asp Ala Glu Ser Leu Ala Gln His Pro Ala
            340                345                350

Ser Met Thr His Ser Ser Tyr Thr Pro Glu Glu Arg Ala His Tyr Gly
            355                360                365

Ile Ser Glu Gly Leu Val Arg Leu Ser Val Gly Leu Glu Asp Ile Asp
            370                375                380

Asp Leu Leu Ala Asp Val Gln Gln Ala Leu Lys Ala Ser Ala
385                390                395

<210> SEQ ID NO 26
<211> LENGTH: 398
<212> TYPE: PRT
<213> ORGANISM: Artificial Sequence
```

<220> FEATURE:
<223> OTHER INFORMATION: G217S enzyme, variant of SEQ ID NO:1, directed to Human L-methionine Gamma-lyase gene.

<400> SEQUENCE: 26

```
Met His Gly Ser Asn Lys Leu Pro Gly Phe Ala Thr Arg Ala Ile His
1               5                  10                  15
His Gly Tyr Asp Pro Gln Asp His Gly Gly Ala Leu Val Pro Pro Val
            20                  25                  30
Tyr Gln Thr Ala Thr Phe Thr Phe Pro Thr Val Glu Tyr Gly Ala Ala
        35                  40                  45
Cys Phe Ala Gly Glu Gln Ala Gly His Phe Tyr Ser Arg Ile Ser Asn
    50                  55                  60
Pro Thr Leu Asn Leu Leu Glu Ala Arg Met Ala Ser Leu Glu Gly Gly
65                  70                  75                  80
Glu Ala Gly Leu Ala Leu Ala Ser Gly Met Gly Ala Ile Thr Ser Thr
                85                  90                  95
Leu Trp Thr Leu Leu Arg Pro Gly Asp Glu Val Leu Leu Gly Asn Thr
            100                 105                 110
Leu Tyr Gly Cys Thr Phe Ala Phe Leu His His Gly Ile Gly Glu Phe
        115                 120                 125
Gly Val Lys Leu Arg His Val Asp Met Ala Asp Leu Gln Ala Leu Glu
    130                 135                 140
Ala Ala Met Thr Pro Ala Thr Arg Val Ile Tyr Phe Glu Ser Pro Ala
145                 150                 155                 160
Asn Pro Asn Met His Met Ala Asp Ile Ala Gly Val Ala Lys Ile Ala
                165                 170                 175
Arg Lys His Gly Ala Thr Val Val Val Asp Asn Thr Tyr Cys Thr Pro
            180                 185                 190
Tyr Leu Gln Arg Pro Leu Glu Leu Gly Ala Asp Leu Val Val His Ser
        195                 200                 205
Ala Thr Lys Tyr Leu Ser Gly His Ser Asp Ile Thr Ala Gly Ile Val
    210                 215                 220
Val Gly Ser Gln Ala Leu Val Asp Arg Ile Arg Leu Gln Gly Leu Lys
225                 230                 235                 240
Asp Met Thr Gly Ala Val Leu Ser Pro His Asp Ala Ala Leu Leu Met
                245                 250                 255
Arg Gly Ile Lys Thr Leu Asn Leu Arg Met Asp Arg His Cys Ala Asn
            260                 265                 270
Ala Gln Val Leu Ala Glu Phe Leu Ala Arg Gln Pro Gln Val Glu Leu
        275                 280                 285
Ile His Tyr Pro Gly Leu Ala Ser Phe Pro Gln Tyr Thr Leu Ala Arg
    290                 295                 300
Gln Gln Met Ser Gln Pro Gly Gly Met Ile Ala Phe Glu Leu Lys Gly
305                 310                 315                 320
Gly Ile Gly Ala Gly Arg Arg Phe Met Asn Ala Leu Gln Leu Phe Ser
                325                 330                 335
Arg Ala Val Ser Leu Gly Asp Ala Glu Ser Leu Ala Gln His Pro Ala
            340                 345                 350
Ser Met Thr His Ser Ser Tyr Thr Pro Glu Glu Arg Ala His Tyr Gly
        355                 360                 365
Ile Ser Glu Gly Leu Val Arg Leu Ser Val Gly Leu Glu Asp Ile Asp
    370                 375                 380
Asp Leu Leu Ala Asp Val Gln Gln Ala Leu Lys Ala Ser Ala
385                 390                 395
```

L-METHIONINE $G(G)-LYASE WITH MODIFIED FUNCTION

This application is the national phase under 35 U.S.C. § 371 of PCT International Application No. PCT/JP01/07271 which has an International filing date of Aug. 24, 2001, which designated the United States of America.

FIELD OF THE INVENTION

The present invention relates to a functionally modified L-methionine γ-lyase, in which an amino acid sequence of the wild type subunit is modified. More particularly, it relates to a recombinant protein constituting a functionally modified L-methionine γ-lyase capable of stabilizing an association of its tetramer and/or its dimer structure of L-methionine γ-lyase; particularly to a functionally modified L-methionine γ-lyase which is improved in various aspects such as, a prevention of the dissociation of a coenzyme, pyridoxal 5'-phosphate (Pyridoxal 5'-phosphate: PLP), a stability in an alkaline solution and a thermal stability thereof. And it relates to a functionally modified L-methionine γ-lyase with increased substrate specificity. It relates to an enzyme consisting a multimer of a recombinant protein constituting a functionally modified L-methionine γ-lyase, an enzyme chemically modified by a stabilizer, a DNA encoding them, a vector including the DNA, a transformant obtained by introducing the vector to the host, and a method of preparation of functionally modified L-methionine γ-lyase comprising a process of cultivation of the transformant and a process of recovering the recombinant protein produced by the culture medium thereof. It relates also to the therapeutic agent comprising functionally modified L-methionine γ-lyase against cancer, obesity, cardiac diseases and the like.

BACKGROUND OF THE INVENTION

L-methionine γ-lyase (EC 4.4.1.11) is an enzyme which requires pyridoxal 5'-phosphate (PLP) as a coenzyme and catalyzes α, γ-dissociation and γ-substitution of L-methionine or its derivatives and also α, β-dissociation and β-substitution of S-substituted L-Cysteine or its derivatives [Tanaka, H. et al., Biochemistry, 16, 100–106 (1977)]. This enzyme has been isolated and purified mainly from *Pseudomonas putida* and its physicochemical and enzymological properties have already been investigated [Nakayama, T. et al., Anal. Biochem., 138, 421–424 (1984)]. Some researches have reported the mechanism of enzymatic reaction catalyzed by L-methionine γ-lyase [Esaki, N. et al., FEBS Lett. 84, 309–312 (1977); Nakayama, T. et al., Biochemistry, 27, 1587–1591 (1988)]. L-Methionine γ-lyase comprises a tetramer of homogeneous subunit (monomer) and one molecular of coenzyme PLP binds to a subunit [Nakayama, T. et al., Biochemistry, 27, 1587–1591 (1988)]. These references are related to enzymes derived from natural source. Further, reported is the preparation of a recombinant enzyme by means of genetic engineering [Inoue, H. et al., J. Biochem., 117, 1120–1125 (1995) and the like, sequence No. 1]. However, the reference does not describe or suggest a functionally modified L-methionine γ-lyase, which is improved in the stability.

It has been reported that the wild type L-methionine γ-lyase purified from a culture of *P. putida* has an anti-tumor activity [WO94/11535, Publication date, May 26, 1994]. Furthermore, It has been suggested that L-methionine γ-lyase may be therapeutic agents for obesity [Orentreich, N et al.; J. Nutr., 123, 265–274 (1993)], Parkinson's disease [Crowell, Jr., et al.; Behav. Neur. Biol., 59, 186–193 (1993)], cardiovascular diseases [Lockwood, B. C. et al.; Biochem. J., Z279, 675–682 (1991)] or aging [Orentreich, N., et al.; J. Nutr., 123, 269–274 (1993)]; [Hoffman, R. N.; Heaman Cell, 10, 69–80 (1997)]. The amino acid sequence and the encoding DNA of L-methionine γ-lyase have been also disclosed [Inoue, et al.; J. Biochem., 117, 1120–1125 (1995)]. The half life of L-methionine γ-lyase in blood of an animal e.g. rat is short, 80 min and extends to only about double even by using a polyethylene glycol modification [Tan, et al.; Protein Expression Purif., 12, 45–52 (1998)]. In this case, the stability of the enzyme may be improved by chemical modification with polyethylene glycol at the Lys residues exposed on the surface of the enzyme. However, the chemical modification at an amino acid residue is completely different from an introduction of mutation. Therefore, the success about the increase of the structural stability of L-methionine γ-lyase with polyethylene glycol does not suggest a success in the increase of the structural stability of L-methionine γ-lyase by substitution, insertion or deletion of the amino acid residues. Furthermore, the chemical modification by means of a stabilizer of protein such as polyethylene glycol and the like did not suggest the further increase of the structural stability of functionally modified L-methionine γ-lyase.

In general, the does of a drug useful for medicines should be small. Accordingly, the supply of a functionally modified L-methionine γ-lyase with an enhanced activity and a long half-time, by means of introduction of a mutation such as substitution of amino acid residue, contributes to the development of a useful anti-tumor agent and the like. The increase in half-life of functionally modified L-methionine γ-lyase is expected by chemical modification with polyethylene glycol and the like. Enhancement of an anti-tumor activity and a reduction of side effects are expected by combining the functionally modified L-methionine γ-lyase and other anti-tumor agents.

DISCLOSURE OF INVENTION

The present inventors have determined steric structure of wild type L-methionine γ-lyase, particularly the site contributing to the preservation of its tetramer structure and the substrate specificity by means of an X-ray analysis for crystal, predicted the amino acid residues for the structure stability and the activity increase, and introduced a mutation, whereby accomplishing the present invention.

The present invention relates to:

(1) A functionally modified protein having at least one mutation selected from mutants; wherein Lys-6 is substituted by His, Gly-9 is substituted by Cys, Cys-49 is substituted by Ser, Cys-116 is substituted by Ser or Tyr, Ala-119 is substituted by Ser, Phe-128 is substituted by Cys, Cys-190 is substituted by Ser, Gly-217 is substituted by Ser, Ser-248 is substituted by Cys, Leu-341 is substituted by His, Asp-382 is substituted by Pro and/or Asp-385 is substituted by Cys, in the amino acid sequence of the subunit of wild type L-methionine γ-lyase described in SEQ ID NO: 1;

(2) The functionally modified protein having a mutation as described in (1) having a mutation, which consists of an amino acid sequence with 85% or more homology of that from No.1 to No. 398 shown in SEQ ID NO: 1;

(3) The protein as described in (1) or (2), wherein its tetramer structure of L-methionine γ-lyase is stabilized;

(4) The protein as described in any one of (1) to (3), wherein the association of each dimer of a subunit of L-methionine γ-lyase is stabilized;

(5) The protein as described in (4), wherein Lys-6 is substituted by His, Lys-395 is substituted by His, Gly-9 and Asp-382 are substituted by Cys and/or Gly-9 and Asp-385 are substituted by Cys, in the amino acid sequence described in SEQ ID NO: 1;

(6) The protein as described in any one of (1) to (3), wherein its dimer structure of a subunit of L-methionine γ-lyase is stabilized;

(7) The protein as described in (6), wherein Cys-116 is substituted by Ser or Tyr, Ala-119 is substituted by Ser, Phe-128 is substituted by Cys and/or Ser-248 is substituted by Cys, in the amino acid sequence described in SEQ ID NO: 1;

(8) The protein as described in any one of (1) to (3), having a mutation for preventing a dissociation of pyridoxal 5'-phosphate, a coenzyme of L-methionine γ-lyase;

(9) The protein as described in (8), wherein Cys-190 is substituted by Ser and/or Leu-341 is substituted by His, in the amino acid sequence described in SEQ ID NO: 1;

(10) The protein as described in any one of (1) to (9), having at least one mutation selected from substitution, insertion or deletion, wherein one or more amino acid residue(s) is (are) to stabilize an association of dimers, to stabilize the dimer structure of a subunit and to prevent a dissociation of co-enzyme, pyridoxal 5'-phosphate;

(11) The protein as described in any one of (1) to (10), having at least one mutation selected from mutation, wherein Lys-6 is substituted by His, Gly-9 is substituted by Cys, Cys-116 is substituted by Ser or Tyr, Phe-128 is substituted by Cys, Ser-248 is substituted by Cys, Leu-341 is substituted by His, Asp-382 is substituted by Cys and/or Lys-395 is substituted by His, in the amino acid sequence, to stabilize the association between dimers and the dimeric structure of the subunit and to prevent the dissociation of the coenzyme, pyridoxal 5'-phosphate;

(12) The protein as described in any one of (1) to (3), wherein the mutation can increase an activity in comparison with that of wild type L-methionine γ-lyase;

(13) The protein as described in (12), having a mutation, wherein Lys-6 is substituted by His, Phe-128 is substituted by Cys, Cys-190 is substituted by Ser, Ser-248 is substituted by Cys and/or Asp-385 is substituted by Cys, in the amino acid sequence described in SEQ ID NO: 1;

(14) The protein as described in any one of (1) to (3), wherein the mutation is to stabilize the enzyme in an alkaline solution;

(15) The protein as described in (14), wherein Cys-49 is substituted by Ser in the amino acid sequence described in SEQ ID NO: 1;

(16) The protein as described in any one of (1) to (3), wherein the mutation is to stabilize the enzyme at high temperature;

(17) The protein as described in (16), having a mutation, wherein Gly-9 and Asp-385 are substituted by Cys in the amino acid sequence described in SEQ ID NO: 1;

(18) The protein as described in any one of (1) to (3), wherein the mutation is to increase substrate specificity of the enzyme;

(19) The protein as described in (18), having a mutation, wherein Gly-217 and Ser-248 are substituted by Cys in the amino acid sequence described in SEQ ID NO: 1;

(20) An enzyme, consisting of a multimer including one or more subunits as described in any one of (1) to (19);

(21) The enzyme as described in (20), comprising a tetramer;

(22) The enzyme as described in (20) or (21), chemically modified by protein stabilizers;

(23) The enzyme as described in (22), wherein a protein stabilizers are polyethylene glycol, dextran, poly N-vinylpyrrolidone, polypropylene glycol, polyoxyethylated polyol, polyvinyl alcohol or glutaraldehyde;

(24) A DNA molecule encoding the protein as described in any one of (1) to (19);

(25) A vector containing a DNA molecule as described in (24);

(26) A transformant obtained by introducing the vector as described in (25) to a host cell;

(27) The transformant as described in (26), wherein the host cell is *Escherichia coli*;

(28) A method of preparing an enzyme as described in any one of (1) to (19), which comprises cultivating the transformant as described in (27) and recovering the produced recombinant protein from the culture medium;

(29) A method of preparing an enzyme as described in (22) or (23), which comprising a chemical modification of a recombinant protein prepared by using the method of preparation as described in (28);

(30) therapeutic agents comprising the enzyme as described in any one of (20) to (23) for cancer, obesity, cardiac diseases, vascular diseases, neurologic diseases or aging.

Furthermore, the present invention relates to (31) a crystalline L-methionine γ-lyase, (32) a structure of L-methionine γ-lyase determined by the X-ray crystal analysis, (33) the structure of crystalline L-methionine γ-lyase and use of the structure to analyze another crystalline state combined with an inhibitor and the like, (34) use of the structure of L-methionine γ-lyase for stabilizing the structure, such as a chemical modification with polyethylene glycol and the like, except for substitution, insertion and deletion of the amino acid residue of wild type or functionally modified L-methionine γ-lyase, and use of functionally modified form.

The present invention as one embodiment relates to a protein characterized by being a functionally modified form of a subunit comprising an amino acid sequence having at least one mutation selected from deletion, substitution or insertion of one or more amino acid residue in the subunit of an amino acid sequence of wild type L-methionine γ-lyase as described in SEQ ID NO: 1. Preferably, the protein is a functionally modified protein having at least one mutation selected from mutations, wherein Lys-6 is substituted by His, Gly-9 is substituted by Cys, Cys-49 is substituted by Ser, Arg-61 is substituted by Lys, Cys-116 is substituted by Ser, Phe-128 is substituted by Cys, Cys-190 is substituted by Ser, Gly-217 is substituted by Ser, Ser-248 is substituted by Cys, Leu-341 is substituted by His, Asp-382 is substituted by Pro and/or Asp-385 is substituted by Cys, in the amino acid sequence described in SEQ ID NO: 1. More preferably, the protein is a functionally modified protein shown by consisting of an amino acid sequence with 85% or more homology with that from No.1 to No. 398 shown in SEQ ID NO: 1. The homology, for instance, can be calculated by the similarity shown as a score which can be obtained by using a search program, BLAST comprising the algorithm developed by Altschul, et al., [J. Mol. Biol., 215, 403–410 (1990).

The term "wild type L-methionine γ-lyase" refers to an enzyme that consists of four subunits (monomers) which comprises a polypeptide having an amino acid sequence represented by SEQ ID NO: 1 [Inoue, H. et al.; J. Biochem., 117, 1120–1125 (1995)] and that has one coenzyme, pyridoxal 5'-phosphate in every subunit. Concretely, two subunits constitute a dimer structure so as to have two coenzymes, pyridoxal 5'-phosphate in the inner side and prevent a dissociation of the coenzyme.

The term "a functionally modified protein of the subunit of L-methionine γ-lyase" refers to a subunit constituting an enzyme that has the same order of biological activity as wild type L-methionine γ-lyase, stabilizes its tetramer structure more than wild type L-methionine γ-lyase and/or has an increased substrate specificity, and refers to a protein that has at least one mutation selected from those having substitution, insertion or deletion of one or more amino acid residue(s).

The term "its tetramer structure of L-methionine γ-lyase is stabilized" comprises "its tetramer structure of L-methionine γ-lyase is stabilized" by stabilizing an association among dimers of the subunit of the enzyme, stabilizing the dimer structure of the enzyme and/or preventing a dissociation of coenzyme, pyridoxal 5'-phosphate, to prevent the enzyme from protease-caused proteolysis and the like in blood.

The term "the association of each dimer of the subunit of L-methionine γ-lyase is stabilized" refers to a protection of the enzyme from protease-caused proteolysis and the like by means of forming a disulfide bond between dimers and can be exemplified by a method, wherein a tetramer structure is stabilized by forming a disulfide bond between dimers by substituting Gly-9 and Asp-385 by Cys and the like, described in SEQ ID NO: 1.

The term "its dimer structure of a subunit of L-methionine γ-lyase is stabilized" refers to preventing the dissociation of the coenzyme, pyridoxal 5'-phosphate by forming a disulfide bond between subunits and protecting a decomposition caused by a protease or the like and is exemplified by a method that stabilizes a dimer structure by substituting Phe-128 by Cys to form a disulfide bond between subunits, by substituting Ser-248 by Cys to form a disulfide bond and by substituting Cys-116 described in SEQ ID NO: 1 by Asp and/or by substituting Ala-119 by Ser to strengthen a hydrogen bond, or the like.

The term "prevent the dissociation of coenzyme, pyridoxal 5'-phosphate" refers to a prevention of an dissociation by means of increasing an interaction between the coenzyme, pyridoxal 5'-phosphate and the subunit, by means of mutation of an amino acid sequence existing in the neighborhood of the binding site of the coenzyme, pyridoxal 5'-phosphate and is exemplified by a method that prevents a dissociation from the subunit by strengthening an interaction with the coenzyme, pyridoxal 5'-phosphate, by substituting Arg-61 by Lys, substituting Cys-190 by Ser and/or substituting Leu-341 by His described in SEQ ID NO: 1. In this method, provided that the substituted amino acid residue is hydrophilic, the dissociation of the coenzyme, pyridoxal 5'-phosphate is prevented owing to hydrogen bonding directly or via a water molecule or an electrostatic interaction. Provided that the substituted amino acid residue is hydrophobic, the dissociation of the coenzyme, pyridoxal 5'-phosphate is prevented by a van der Waals interaction.

The term "increase an activity in comparison with that of wild type L-methionine γ-lyase" refers to enhancing activity of the modified form comparing with that of the wild type form under the same condition of measurement and is exemplified by a method stabilizing the structure of an enzyme, increasing the specificity of a substrate or preventing a dissociation of PLP thereof by substituting Lys-6 by His, substituting Phe-128 by Cys, substituting Cys-190 by Ser, substituting Ser-248 by Cys and/or Asp-385 substituting by Cys described in SEQ ID NO: 1.

The term "stabilize the enzyme in an alkaline solution" refers to preventing the decrease of the enzymatic activity at a higher pH than the optimum pH of the enzyme and is exemplified by a method which prevents an aggregation of enzyme by stabilizing the structure of the enzyme, preferably its tetramer structure or the like, thereof by substituting Cys-49 by Ser described in SEQ ID NO: 1.

The term "stabilize the enzyme at high temperature" refers to preventing the decrease of the enzymatic activity at higher temperature than the optimum temperature of the enzyme and is exemplified by a method which increases the thermal stability by stabilizing a structure of the enzyme, preferably by stabilizing an association between subunits by substituting Gly-9 and Asp-385 by Cys, described in SEQ ID NO: 1.

The term "increase substrate specificity of the enzyme" refers to increasing the enzymatic activity by enhancing a substrate specificity by substituting a site that recognizes the substrate, L-methionine, to an amino acid residue, which can easily associate with the substrate and is exemplified by a method, wherein a specificity to L-methionine increases by substituting Gly-217 by Ser and/or substituting Ser-248 by Cys described in SEQ ID NO: 1.

Some of various possible substitution, insertion and deletion by some of many permissible amino acids may result in producing unfavorable effects on an enzymatic activity. Such a substitution, insertion or deletion by amino acids for strengthening the structure around the binding site between an enzyme and a coenzyme and the steric structure, may result in decreasing both an affinity to L-methionine and decomposition rate. But it is possible to select modified enzymes without a remarkable decrease in the activity by testing the L-methionine-decomposition activity of a functionally modified L-methionine γ-lyase.

The present invention provides a method for preparing a functionally modified L-methionine γ-lyase which comprises constructing a recombinant vectors by introducing a DNA sequence encoding the functionally modified L-methionine γ-lyase which is modified by substitution, insertion or deletion of the above amino acid in the amino acid sequence described in SEQ ID NO: 1, introducing it into a vector suitable for a host, transforming the host with the vector and cultivating the transformant. The present method can be carried out according to the steps as exemplified below. Once the DNA sequence coding L-methionine γ-lyase is disclosed by the present invention, certain steps can be omitted or simplified by one ordinary skilled in the art.

BEST MODE FOR CARRYING OUT THE INVENTION

Figure 1:
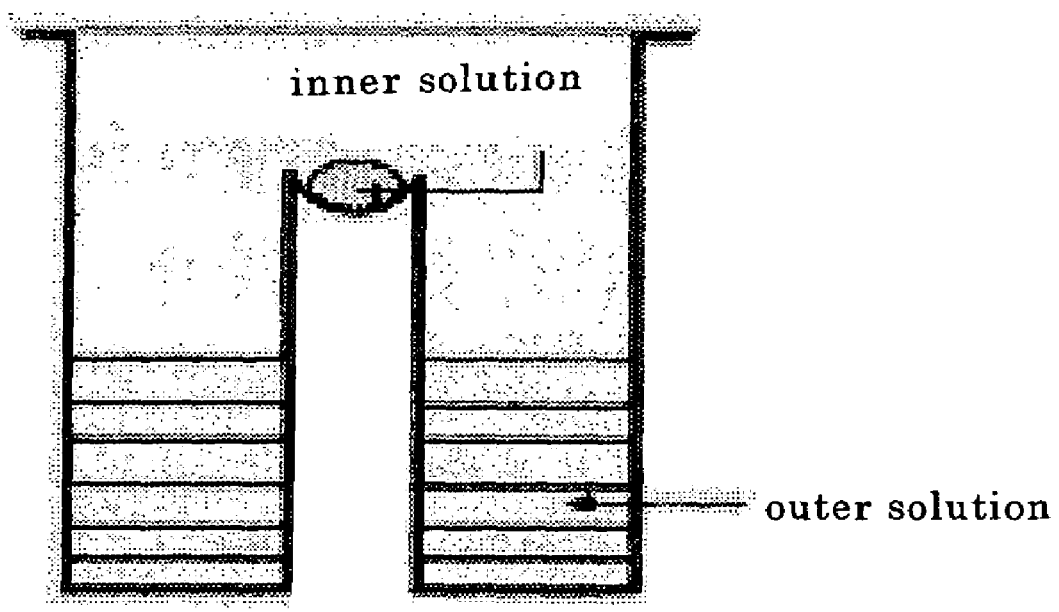
FIG. 1 shows a schema of vapor diffusion method (Sitting Drop method).
Figure 2:
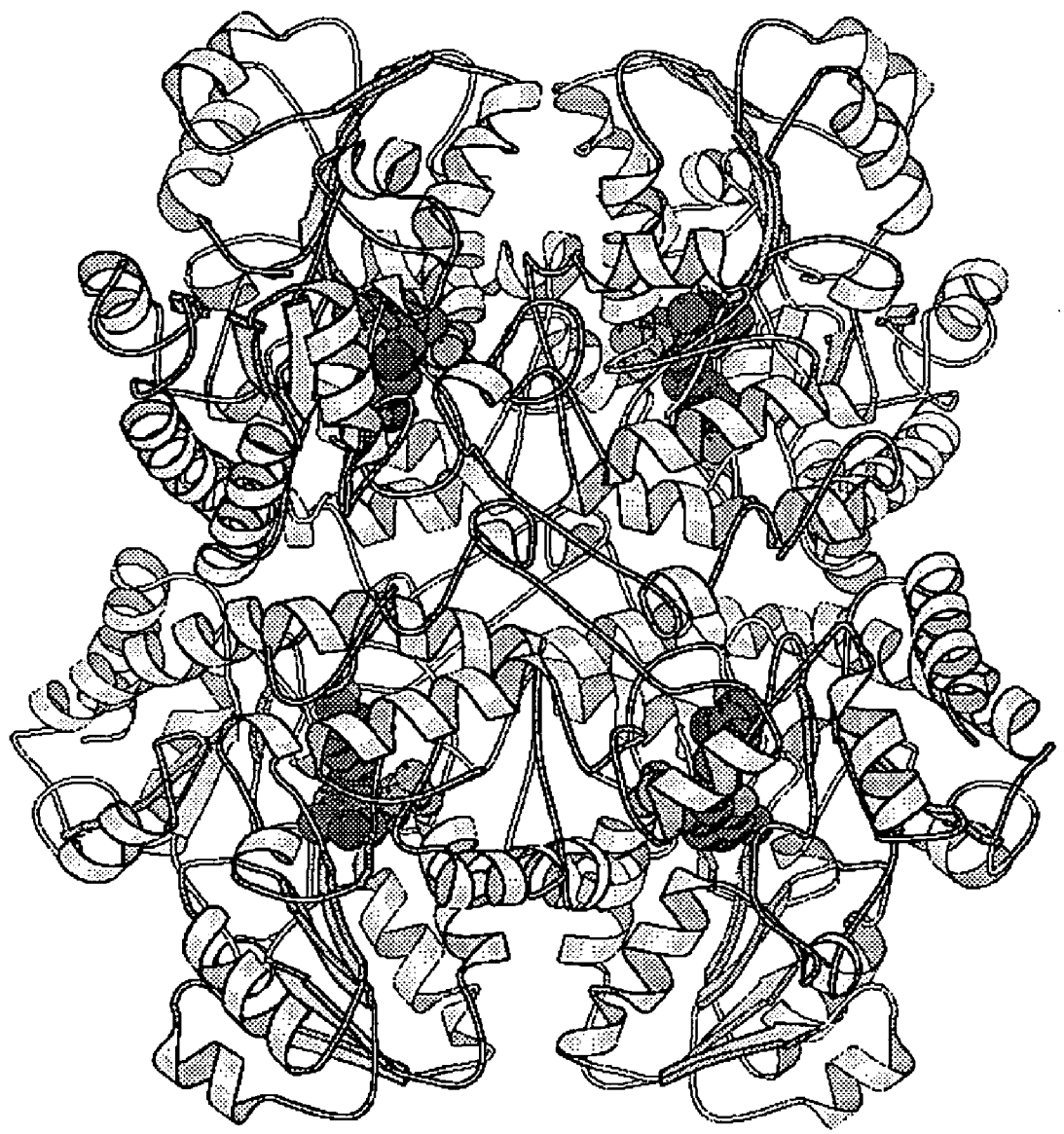
FIG. 2 is a schema of a tetramer structure of L-methionine γ-lyase. Its tetramer comprises four subunits, each of which binds to one coenzyme, pyridoxal 5'-phosphate. Pyridoxal 5'-phosphate is shown with black color.
Figure 3:
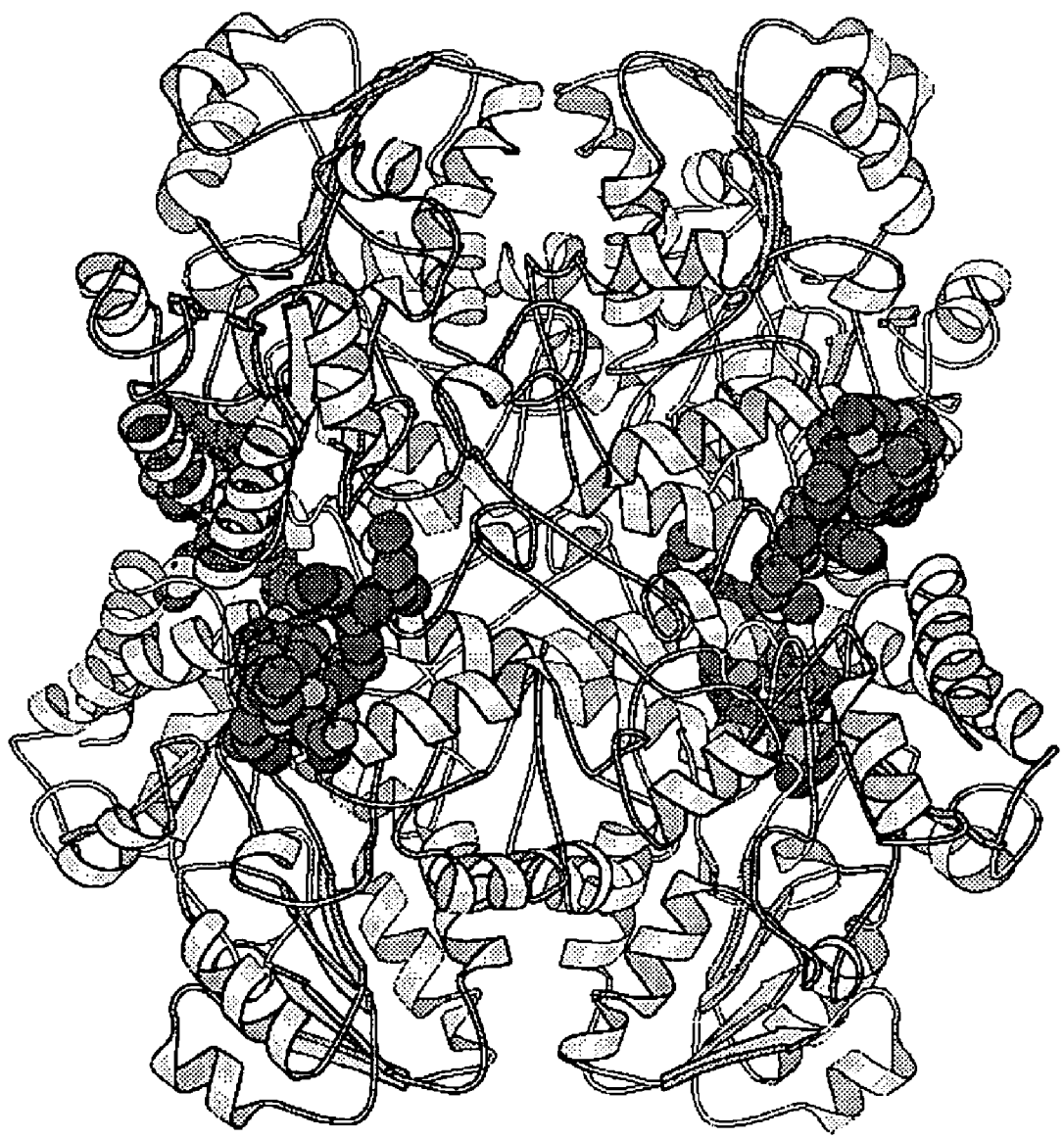
FIG. 3 shows 10 amino acid residues of the N-terminal of the amino acid sequence of each subunit in its tetramer structure of L-methionine γ-lyase with black color.
Figure 4:
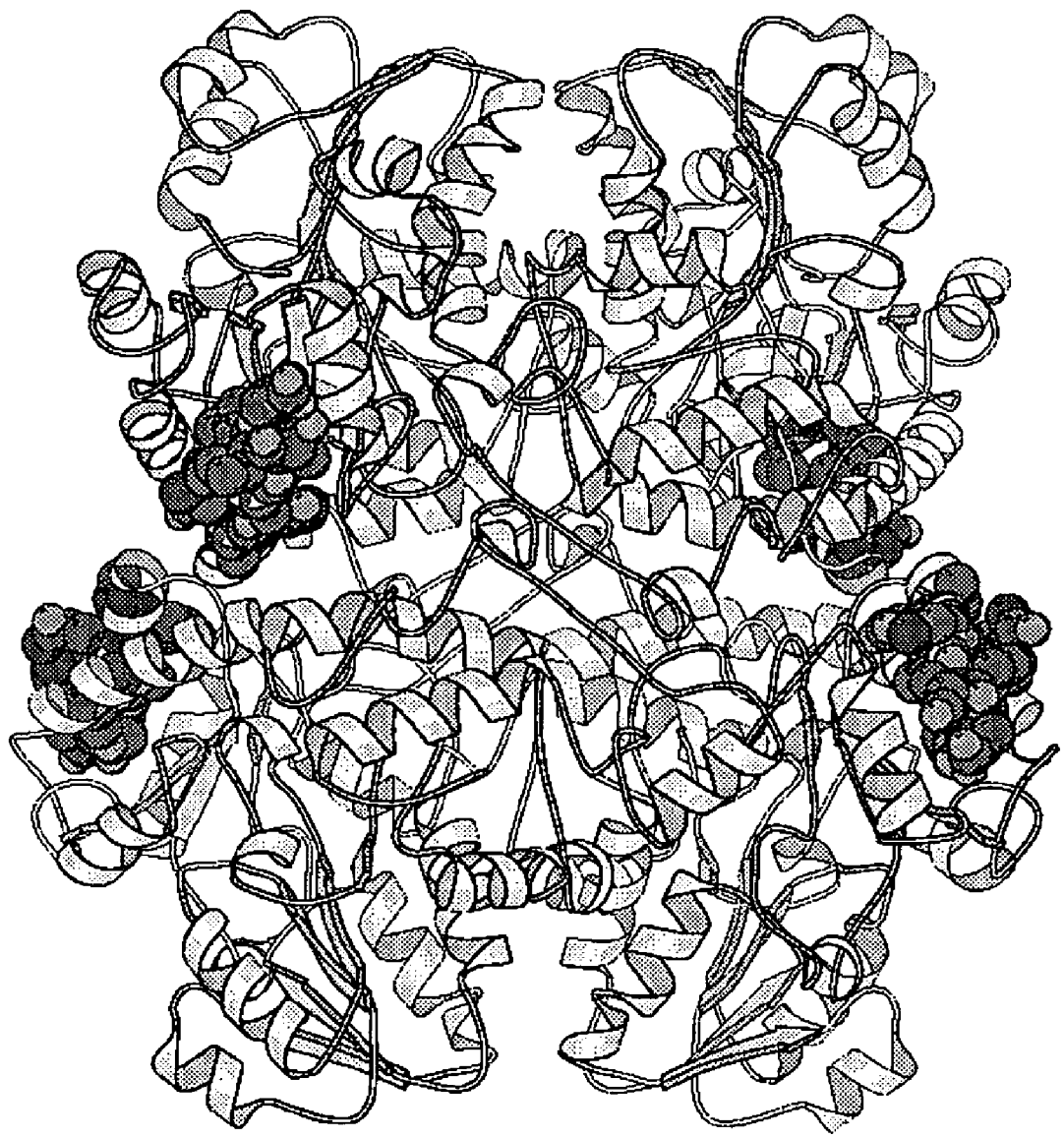
FIG. 4 shows 10 amino acid residue of the C-terminal of the amino acid sequence of each subunit in its tetramer structure of L-methionine γ-lyase with black color.
Figure 5:
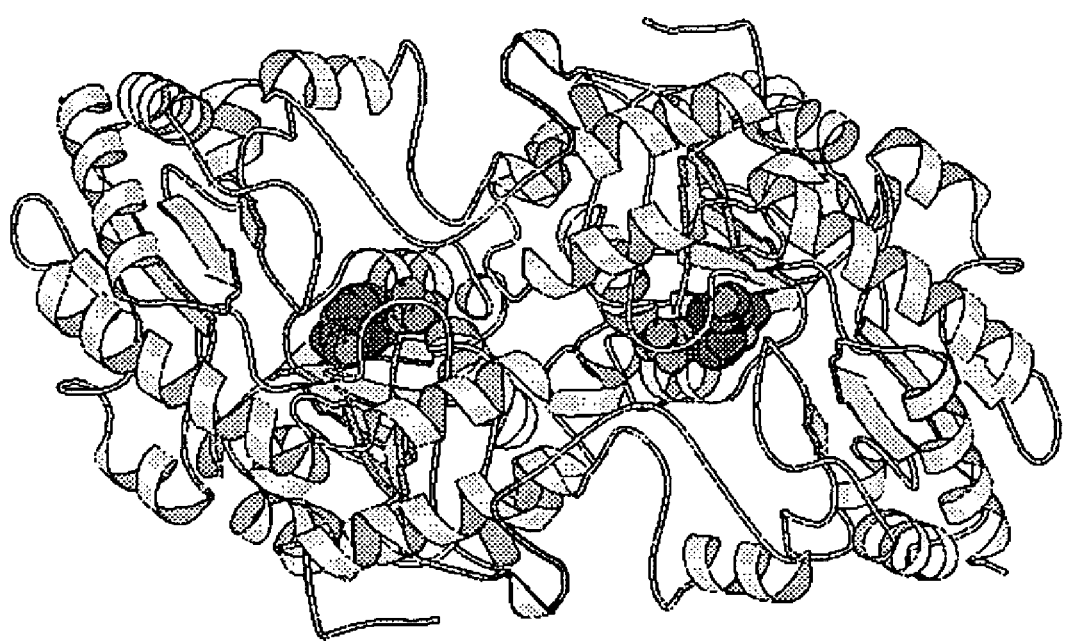
FIG. 5 is a schema of a dimer structure of L-methionine γ-lyase. Each subunit binds to the coenzyme, pyridoxal 5'-phosphate and they interact each other in the dimer. The coenzyme pyridoxal 5'-phosphate is shown with black color.
Figure 6:
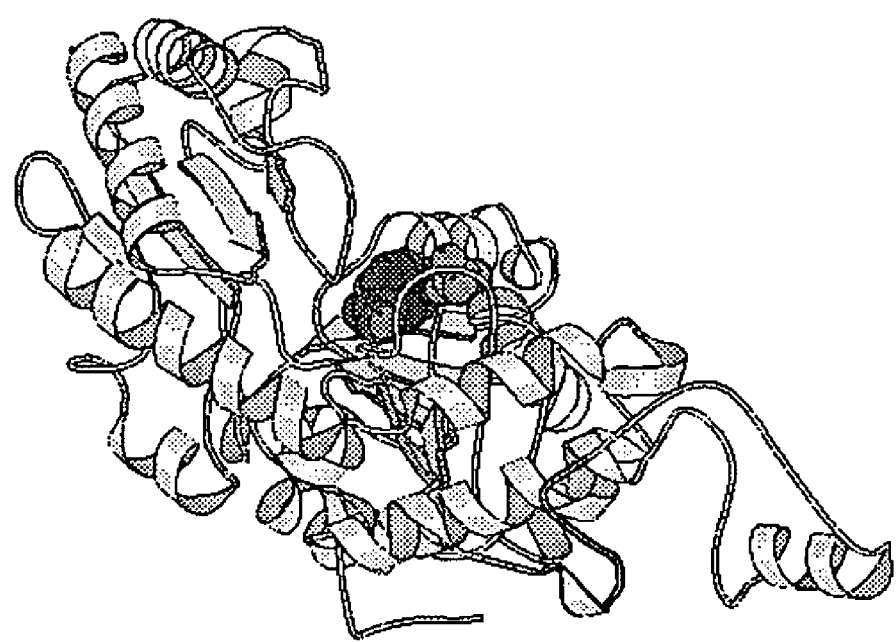
FIG. 6 is a schema of a monomer structure of L-methionine γ-lyase. The subunit binds to the coenzyme, pyridoxal 5'-phosphate.
Figure 7:
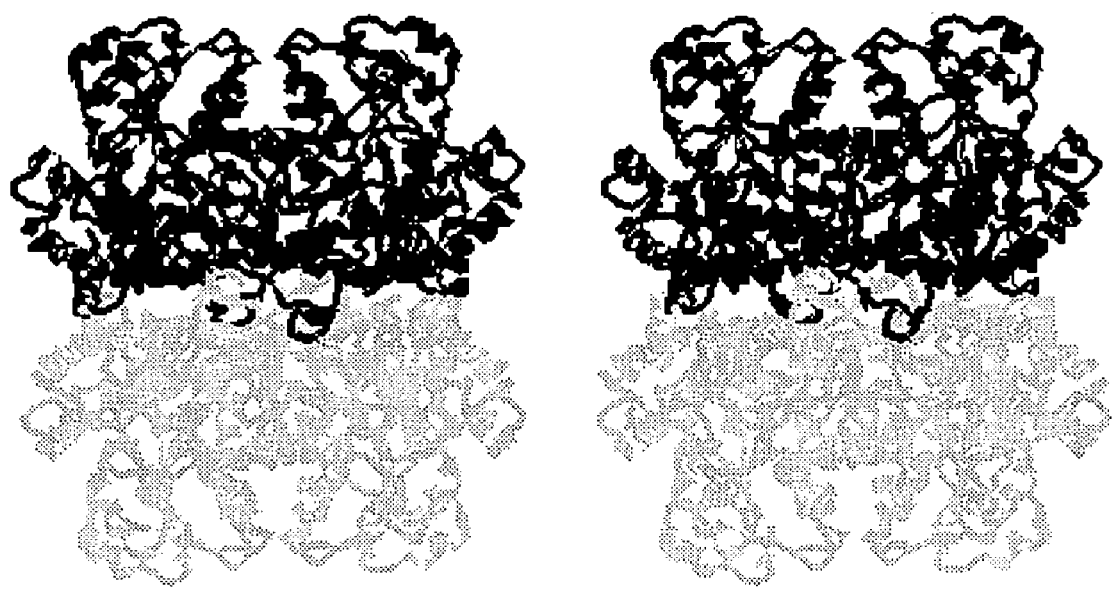
FIG. 7 shows an association among dimers in the tetramer structure of L-methionine γ-lyase.
Figure 8:
FIG. 8 shows an association between monomers in the dimer structure of L-methionine γ-lyase.
Figure 9:
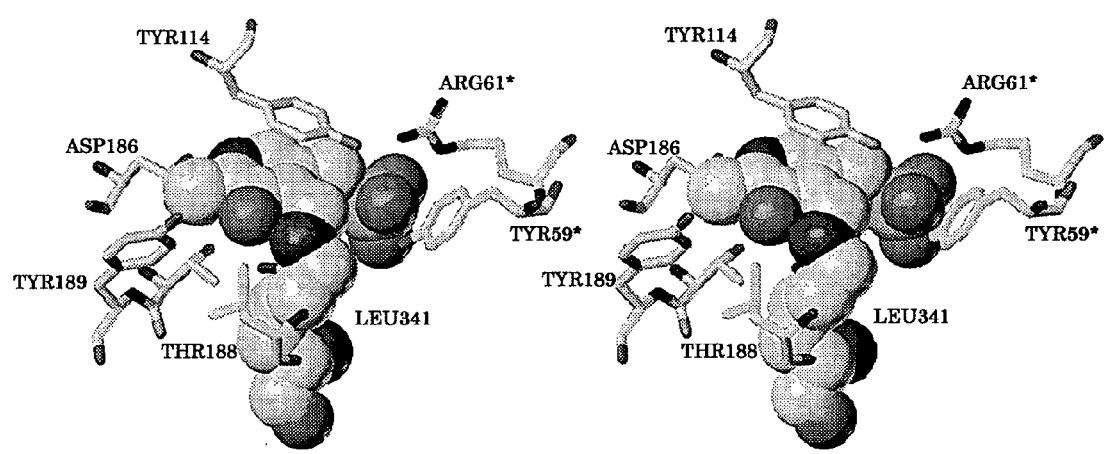
FIG. 9 shows a binding site of the coenzyme, pyridoxal 5'-phosphate in the dimer structure of L-methionine γ-lyase.

The present invention is explained in more detail below

Preparation of Crude L-Methionine γ-Lyase Solution

According to the procedure described in J. Biochem., 117, 1120–1125 (1995), a strain which expresses L-methionine γ-lyase is prepared by introducing a recombinant plasmid containing the region of structural gene of L-methionine γ-lyase into E. coli cells and is cultivated. From the resulting culture broth, cells are harvested, disrupted, and an aqueous solution of polyethyleneimine is added to adjust the final concentration of the solution to 0.05 to 0.5% (w/v), preferably 0.1 to 0.2% (w/v). Then, the solution is treated at 5 to 25° C. for 1 to 20 min for removing cell debris to obtain a solution of crude L-methionine γ-lyase. The cell debris may be removed by heat treatment (at 55 to 65° C. for 1 to 10 min) of the supernatant obtained by discarding the harvest of the cell by a centrifugation, instead of the treatment with the aqueous polyethyleneimine. The cell debris may be removed by adding a filter aid such as Coporoc-SA. The solution of the crude enzyme is subjected to salt-out with ammonium sulfate and then centrifugal separation. The obtained precipitate is dissolved in a buffer solution, preferably in a phosphate buffer to prepare a solution of crude L-methionine γ-lyase can be prepared by dissolving. The concentration of L-methionine γ-lyase in the phosphate buffer is 4 to 30 g/L, preferably 10 to 20 g/L and most preferable is 15 g/L at this stage.

The impurity is removed by adding polyethylene glycol to the solution of crude L-methionine γ-lyase so as to be 5 to 25% (w/v), preferably 8 to 12% (w/v) in the final concentration, followed by stirring at 2 to 15° C., preferably 4° C. for 10 to 120 min, preferably 60 min. Preferable polyethylene glycol is about 7200 or more in average molecular weight such as PEG 6000 and the like. To increase the concentration and to minimize a loss of L-methionine α-lyase, ammonium sulfate is added so as to be a 8 to 12% solution in the final saturated concentration, preferably 10% or the pH value of the solution is adjusted to be 7.5 to 9.5, which is far from the isoelectric point of L-methionine γ-lyase, preferably 8.0 to 9.0.

Preparation of Crude Crystals of L-Methionine γ-Lyase (1) A solution containing L-methionine γ-lyase, preferably that obtained after removing the impurity in the above-mentioned process 1 is warmed and polyethylene glycol is added. Warming may be carried out before or after the addition of polyethylene glycol, preferably before the addition. Furthermore, polyethylene glycol may be added both of before and after the warming and in this case, the addition of polyethylene glycol before the warming may be also for removing the above mentioned impurity. The temperature after the warming is 25 to 40° C., preferably 32° C. Polyethylene glycol may be added according to a usual manner based on a crystallization method for protein and preferable is that polyethylene glycol of more than 7200 in average molecular weight is used and added so as to be a 5 to 25% (w/v) solution in the final concentration, followed by stirring to dissolve.

(2) Rod crystals of L-methionine γ-lyase are prepared by adding inorganic salts to the above solution. The inorganic salt is preferably an alkaline metal salt and exemplified by sodium chloride, potassium chloride and the like, most preferable is sodium chloride. The inorganic salt is preferably used in the final concentration of 20 to 500 mM, more preferably of 100 to 200 mM. The crystal appears without stirring, but preferably stirring is continued during the above mentioned procedure (1) or (2). The pH value of the solution for preparing the crystal is preferably at pH 7.0 to 8.0, more preferably pH 7.2 to 7.5. Thus, the appeared crystal of L-methionine γ-lyase can be collected, for example by using a centrifuge or the like.

The obtained crude crystal of L-methionine γ-lyase had high purity and a decrease of pyrogenic substances was observed. The crystal can be preserved for a long period under a cold condition. By dissolving the crystals again and then repeating the above mentioned procedures (1) and (2), a recombinant L-methionine γ-lyase can be obtained, which is purified the same as or more than that obtained by purification using in combination without crystallization. In addition to the present purification method including the preparation of the crystals, purification method of column choromatography, such as ion exchange chromatography or gel filtration chromatography, and can give an enzyme of high purity with the very little impurity protein, and the pyrogenic substance therein is at very low concentration suitable for the medicine approval. In the economic manufacturing, the crystallization method is obviously favorable than the chromatography. Then, the purification method of L-methionine γ-lyase including the preparation of the crystal of the present invention is a very useful industrial purification method.

Preparation of the Crystal of L-Methionine γ-Lyase

Crystallization of the enzyme for the X-ray experiment can be performed using a solution of L-methionine γ-lyase. A vapor-diffusion method, e.g. Hanging Drop, Sitting Drop or the like, or a dialysis method can be used as a crystallization method. Every method comprises the realization of the equilibration between the solution containing the protein (inner solution) and that without the protein (outer solution), to accelerate the supersaturation and the growth from the crystal of the solution. The vapor-diffusion method is that the inner and outer solutions do not contact directly and the dialysis method is that the inner and outer solutions can contact through the dialysis membrane, which has an ability to cut molecules of an appropriate weight. In crystallization of L-methionine γ-lyase, one of the vapor-diffusion methods, Sitting Drop method was used. Condition of crystallization is searched using a general method in this field. That is, kinds and conditions such as buffers, precipitating agents, additive agents, crystallization temperature are considered and performed under various systems. The crystallization was carried out using a phosphate buffer, HEPES buffer, Tris buffer or the like as the buffer solution, PEG, MPD or the like as the precipitating agent and ammonium sulfate, sodium chloride, lithium chloride or the like as the additive agent.

A solution for crystallization 1 was prepared by adding, to a 50 mM solution of phosphoric acid adjusted to pH 7.1 to 7.5, preferably pH 7.2, ammonium sulfate so as to be a 0.5 to 1.5% solution (w/v), preferably 1% (w/v) and adding MPD so as to be a 40% solution. Then a solution for crystallization 2 was prepared by adding ammonium sulfate so as to be a 0.5 to 1.5% solution (w/v), preferably 1% (w/v) and adding PEG 6000 so as to be a 28 to 32% solution, preferably 30%, to a 50 mM solution of phosphoric acid adjusted to pH 7.1 to 7.5, preferably pH 7.2. To a solution containing L-methionine γ-lyase, 9.5 to 10.5 μl, preferably 10 μl which was filtrated using a centrifugal separator or the like, the solution for crystallization 1, 490 to 510 μl, preferably 500 μl and the solution for crystallization 2, 9.5 to 10.5 μl, preferably 10 μl are added The mixture is mixed slowly and used as an internal fluid. The internal fluid is added to a plate for crystallization and immediately the plate is allowed to stand in a chamber at 3 to 5° C., preferably 4° C. to obtain crystals suitable for the X-ray crystallography.

The crystals of recombinant L-methionine γ-lyase obtained through such a crystalline method had the same order of enzymatic activity as that of the corresponding wild type protein even after dissolving again. And the amino acid sequence of the N terminal was identical each other.

Structure Analysis of a Crystal of L-Methionine γ-Lyase

The diffraction intensity of crystals was measured by using an X-ray detector such as the detector system R-AXIS IV equipped with the imaging plate (Rigaku Co.), an imaging plate or a CCD, at Beamline 24XU-hatch A (Hyogo prefecture's beamline) of synchrotron radiation facility, Spring-8 in Japan. X-ray, produced from an X-ray generator of circulated anti-cathode systems or the synchrotron radiation, is irradiated to the crystal, whose diffraction patterns are obtained. The obtained diffraction patterns are processed and scaled as an intensity data set by using software programs for treatment of diffraction patterns such as DENZO (HKL Research Inc.), and then structure determination is carried out. A program package, X-PLOR [A. T. Brunger, X-PLOR, Version 98.0: Yale University press: New Haven, Conn., 1998; offered by Molecular Simulations, Inc. and the like] is used to determine the steric structure. Generally, the crystal structure, wherein the R value is 25% or less and the resolution is 2 to 3 Å, can be obtained by the data of the synchrotron radiation and an imaging plate system and by refinement using X-PLOR. This quality is enough for the identification of inhibitors.

The stereo view of the complex of the apoenzyme and the coenzyme can be achieved using software for a graphic computer such as Insight II [Biosyn/molecular simulations, Inc. (San Diego, Calif.)], Quanta [Molecular Simulations, Inc. (Burlington, Mass.)] or the like. The geometries of the interactions mode between the apoenzyme and the coenzyme can be clarified by using tools included in the program. A crystal of L-methionine γ-lyase was prepared by Sitting Drop method from the protein solution of phosphate buffer pH 7.2 with MPD, PEG 6000 and ammonium sulfate as precipitants. The diffraction patterns from the crystal was measured by using the X-ray diffraction system equipped with an imaging plate, R-AXIS IV (Rigaku Co.) and reflections were collected until 1.8 Å resolution. The structure was determined by the molecular replacement method using the routine of the program package, X-PLOR. The R-value of refinement structure is 23.4%. The space group of the crystal was $P4_32_12$ (Z=32). There were independent 4 molecules in an unsymmetrical unit and the each molecule built local 222 symmetry each other. Coenzyme, PLP locates around the borderline of the dimer forming the tetramer and interacts with the two molecules in the dimer, which is built with local diad. The measured diffraction patterns from the crystal was processed with software, DENZO (HKL, Research Inc.).

Functionally Modified L-Methionine γ-Lyase

The present invention also provides a method of preparing a functionally modified L-methionine γ-lyase and of determining the crystal structure. In more detail, the present invention provides a method of identifying the active site by determining the position of the association site of the dimer and the subunit and the position of the binding site of pyridoxal 5'-phosphate, based on the crystal structure of L-methionine γ-lyase. For example, functional modification can be carried out at the specified or combined site among sites of association of the dimer and the subunit, and the binding site of pyridoxal 5'-phosphate. The functionally modified form is characterized by some special properties different from that of wild type of L-methionine γ-lyase. For example, the functionally modified form may have an increased structural stability toward the dissociation of the subunit.

(1) The protein of the present invention, a functionally modified L-methionine γ-lyase in can be prepared by various methods. For example, the wild type amino acid sequence of L-methionine γ-lyase can be mutated by means of the induction of specific mutation to oligonucleotide or another previous technique such as deletion at the desired site, which was found suitable for the functional modification by the present invention. The functional modification can be introduced into the DNA sequence encoding L-methionine γ-lyase by using synthesized oligonucleotide. These oligonucleotides include a neighboring nucleotide sequence at the desired functionally modified site. The mutation of the amino acid sequence for the functionally modification can be obtained by introducing a mutation into an optimal sequence encoding the full-length DNA sequence of L-methionine y-lyase.

(2) The DNA sequence of a functionally modified L-methionine γ-lyase which is produced using the above mentioned method or conventional used technique in this field, can be expressed by the present invention using an expression vector. As is well known in this field, the expression vector includes an autonomously replicable element in the host cell independent from the host genome and one or more markers of phenotype for selective purpose. Before or after the insertion of the DNA sequence including the DNA sequence encoding desired a functionally modified L-methionine γ-lyase, the expression vector may also include promoter, operator, ribosome binding site, translation initiation signal or at need repressor gene, various activator genes, regulatory sequence encoding termination signal or the like. When secretion of the functionally modified protein produced is desired in some embodiments, the nucleotide encoding "signal sequence" may be introduced into the former part of the DNA sequence encoding a functionally modified L-methionine γ-lyase. The desired DNA sequence must be bound to the regulatory sequence so as to operate, to express it under a control of the regulatory sequence. That is, an appropriate initiation signal must exist before the DNA sequence maintaining suitable leading frame, which encodes a functionally modified L-methionine γ-lyase and makes it possible to express the sequence under a control of the regulatory sequence and to produce the desired product encoded by the sequence of L-methionine γ-lyase.

(3) Various well-known expression vectors are useful to express the sequence of a functionally modified L-methionine γ-lyase of the present invention. These include for example SV40 and the derivatives, a well-known bacterial plasmid e.g. a plasmid originated from *Escherichia coli* including colE1, pCR1, pBR322, pMB9, their derivatives and the like, a plasmid of more wide host area, e.g. RP4, phage DNA, e.g. many λ phage derivatives such as NM989, a DNA phage such as M13, a fibrous DNA phage of a single strand and the like, a plasmid of yeast, e.g. 2μ plasmid or the derivative and the vector obtained from combining the plasmid with phage DNA, e.g. phage DNA or a chromosomal DNA sequence such as a plasmid modified to use other express regulatory sequences, a non-chromosomal DNA sequence, a segment of synthesized DNA sequence and the like. Preferable is an expression vector for *Escherichia coli*.

(4) When the expression vector is bound to the DNA sequence encoding the functionally modified protein so as to work well, various optional expression regulatory sequences that regulate the expression, can be used in the expression vector to express the DNA sequence encoding the functionally modified protein of the present invention. These expression regulatory sequences refer to an early or late promoter sequence of SV40 for animal cell, lac promoter, trp promoter, tac promoter, trc promoter or the like, a main operator or promoter region of a λ phage regulatory region of a fd coat protein, a promoter sequence of a 3-phosphoglycerate kinase or another glycolytic enzyme, a promoter sequence of a acidic phosphatase such as Pho5 and the like, a promoter sequence of an α-mating factor of yeast, another well-known sequences regulating gene expression of procaryote, eukaryote, their virus or the like, their combination or the like. In a preferable embodiment of the present invention, the inventors use the expression regulatory sequence useful for hosts, *Escherichia coli* or a cell strain of kidney of monkey COS-1.

(5) Various kinds of host cells transformed by the expression vector can be used and they are useful for the preparation of a functionally modified L-methionine γ-lyase of the present invention. A procaryote, a unicellular eukaryote such as yeast, an animal cell, a plant cell and an insect cell are exemplified as the host.

The procaryote is the cell belonging to the genera of *E. coli, bacillus, streptomyces* and the like and is exemplified by *Escherichia coli, Bacillus subtilis* and the like. The yeast is the strain belonging to the *Saccharomyces, Schizosaccharomyces* and the like and is exemplified by *Saccharomyces cerevisiae, Schizosaccharomyces pombe* and the like. The animal cell is exemplified by 293 cell originated from human fetus kidney, COS-7 cell originated from an African green monkey kidney, a CHO cell originated from a Chinese hamster ovary and the like. The plant cell is exemplified by a cell originated from cigarette, potato, wheat and the like. The insect cell is exemplified by Sf9 and SF21 cells originated from *Spodoptera frugiperda* ovary and the like. Preferably used are genus of *E. coli*, e.g. JM109 strain of *Escherichia coli* and COS-1 cell of animal cell.

In case that the DNA sequence encoding functionally modified L-methionine γ-lyase of the present invention is expressed to prepare the protein, it should be noted that all of the expression vectors and the expression systems do not always function in the same way. All of the hosts do not always function well with the identical expression system. However, a person ordinary skilled in the art can select the vector, an expression regulatory sequence and a host, without experiments and within the scope of the present invention. For example, an important thing to be considered in the selection of the vector is the replication ability of the vector for a host. Furthermore, the copy number, the regulatory ability of the copy number or the antibiotic resistant marker and the like which expressed other proteins encoding in the expression vector must be considered. When the expression regulatory sequence is selected, various kinds of factors must be considered, e.g. relative strength of the system, regulatory ability, compatibility with the DNA sequence encoding functionally modified L-methionine γ-lyase of the present invention and especially compatibility with a potential secondary structure and the like.

(6) The host should be selected considering a compatibility with the selected vector, a toxicity of functionally modified L-methionine γ-lyase to the host, a secreting ability of matured products, an ability to fold a protein appropriately, an ability to form its tetramer, an requirement for fermentation, easiness of the purification of functionally modified L-methionine γ-lyase and safety thereof. A person ordinary skilled in the art can select, these parameters, a combination of various kinds of vectors, expression regulatory systems and hosts, that can produce an effective amount of functionally modified L-methionine γ-lyase. The functionally modified L-methionine γ-lyase produced by using these systems can be purified through the various kinds of processes or strategies including those used for the purification of wild type L-methionine γ-lyase. Once a mutation is inserted mutation at the desired position of L-methionine γ-lyase, that is, at the active site or the auxiliary binding site, the mutant can be examined in some specific characters. Such a mutant includes those obtained for example by a dissociation of the dimer, a dissociation of the monomer, a dissociation of pyridoxal 5'-phosphate, an increased stabilities for both pH and temperature, an increased substrate specificity and the like.

Examples are described below to understand the present invention more completely. These examples are intended to illustrate the present invention in more detail and not to be construed to limit the scope of the present invention.

The technique of gene engineering in examples can easily be carried out according to a well-known method in this field. The above mentioned process can be operated easily by the procedure cited in the direction for experiments, for example, Molecular Cloning: A Laboratory Manual, 2nd Ed. Vol. 1–3, Sambrook J. et al., Cold Spring Harbor Laboratory Press, New York (1989). All of the reagents used, e.g. enzyme, buffer, culture medium and the like, are commercially available can be used under the designated condition, unless otherwise noted.

A determination method of the amino acid sequence of protein is well known in the above process (1), for example, an automatic amino acid sequencer on the market can be used. The synthesis of oligonucleotide having a specified base sequence can be carried out by using a DNA synthetic apparatus on the market according to the operating procedure in the process (1) and (2). The DNA base sequence can be determined using a well-known M13 vector by the method of Snger, et al. [Proc. Natl. Acad. Sci. U.S.A., 74, 5463–5467(1977)] in the process (1) and (2).

The vector for cloning refers to a plasmid vector such as pUC118, pUC119, pUC13, pBR322 or pAT153 or a phage vector such as λZAPII, λgt10 in the process (1) and (2). An E. coli bacteria can be used as a host for cloning and expression, e.g. Escherichia coli K-12 cell line, such as HB101 strain, DH1 strain, C600 strain, JM103 strain, JM105 strain, JM109 strain or MV1184 strain. When yeast is used as the host for the expression of functionally modified protein of the present invention, pYES2, pYEUra3 and the like can be used as the vector for isolation of the protein from the supernatant. When pseudomonas strain is used as the host, RSF1010, RK2 and the like can be used as the vector and so called self-cloning can be performed. These vectors and hosts are commercially available.

To prepare the plasmid having effective expression ability of the desired gene in E. coli in the above process (3) and (4), a DNA fragment containing the structural gene of intended functionally modified L-methionine γ-lyase may be inserted into a promoter suitable for a function in the host such as Lac, Tac, Trc, Trp and λPL, an expression vector having Shine-Dalgarno (SD) sequence e.g. pKK223-3 and pPL-lambda and the like, and furthermore an ATG vector having a translation initiation codon ATG e.g. pKK233-2, pTrc99A and the like.

The effective expression may be possible by inserting the constructed expression plasmid into a suitable host, e.g. Escherichia coli, JM103 strain, JM109 strain, HB101 strain, C600 strain or the like in the above process (5).

Purification and isolation of the expressed functionally modified L-methionine γ-lyase can be carried out by combining various well-known methods of purification and isolation in the above mentioned process (6). The well-known method refers to salting-out, dialysis, ultrafiltration, gel filtration, various kinds of chromatographies such as ion-exchange chromatography and the like, various kinds of electrophoresis such as SDS-polyacryl amide gel electrophoresis and the like.

The protein defined by the term "a protein of functionally modified form of the subunit, comprising an amino acid sequence having at least one mutation selected from substitution, insertion or deletion of one or more amino acid residue is in comparison with the subunit of an amino acid sequence of wild type L-methionine γ-lyase as described in SEQ ID NO: 1" means a functionally modified protein which can include a chemical or biochemical modification as well as natural or unnatural amino acid or the amino acid sequence, provided that the formation or activity is the substantially same as L-methionine γ-lyase produced by pseudomonas putida ICR3460 cell line. The functionally modified protein can be prepared by a well-known method by a person ordinary skilled in the art such as a site-specific mutagenesis using the PCR method.

Accordingly, the present invention also provides an anti-tumor agent comprising the functional modified L-methionine γ-lyase of the present invention or variants thereof. The anti-tumor agent of the present invention can be prepared using any of known carriers or excipients therefor. It is typically in the form of injections and can be lyophilized products. For administration, it will be generally infused parenterally over several ten minutes to several hours per day for several days to several weeks. Although the administration dose varies depending on intended effects, sex, age, weight and severity of symptoms of patients and the like, it is generally from about 1 to 1000 U/kg weight/day, and preferably from about 50 to 500 U/kg weight/day.

EXAMPLE

The following Examples and reference examples further illustrate the present invention in more detail but are not to be construed to limit the scope thereof.

Example 1

Cultivation of Expression Strain of L-Methionine γ-Lyase

The region of the structural gene of L-methionine γ-lyase was inserted into the expression vector of pKK233-2 and the expression plasmid of L-methionine γ-lyase, pMGLTrc03 was inserted into an E. coli, JM109 strain, which was used for the expression strain of recombinant L-methionine γ-lyase. After the first pre-culture in a LB medium and then second preculture in a LB medium containing 0.5% glycerin, the cells were cultivated at 28° C. for 24 h in a Terrific medium containing 4% glycerin on three 30-L jar fermenters. Isopropyl-β-D-thiogaractopyranoside was added so as to be a 0.3 mM solution at the logarithmic growth phase to induce the expression of L-methionine γ-lyase.

Example 2

Preparation of the Crude Enzyme Solution

The culture broth of the recombinant bacteria obtained in Example 1, 57 kg was separated by a centrifugal separator (Alfalaval Co.) to give a concentrated cell suspension, 19 kg. 100 mM phosphate buffer (pH 7.5) 17.4 kg containing EDTA 24.57 g, pyridoxal 5'-phosphate (PLP) 10.34 g and dithiothreitol (DTT), 3.3 g were added to the concentrated cell suspension. The suspension of cells was warmed at 28° C. and the cell was disrupted by the use of a high pressure homogenizer (APV Gaulin, Inc.). A filter aid, Coporoc-SA (Otsuka Pharmaceuticals Co.) was added to the disrupted cell suspension, 36.6 kg so as to be a 0.6% solution (w/w) in the final concentration and the mixture was stirred for 1 h. A centrifugal separation of the mixture 39 kg treated with coprec-SA gave a solution of the crude enzyme 37 kg, in which there was L-methionine γ-lyase 160 g of specific activity 29 U/mg.

Example 3

Preparation of Crude Crystals of L-Methionine γ-Lyase

Ammonium sulfate 8.86 kg was added gradually to a solution of the crude enzyme obtained in Example 2 so as to be a 40% saturated ammonium sulfate solution. The mixture dissolved at pH 7.2 with aqueous ammonia, was salted out at 4° C. and preserved for 1 to 3 days. Separation by centrifuging, a precipitate, was dissolved in a dissolving buffer (20 mM phosphate buffer, pH 7.2; 0.5 mM PLP, 0.05% 2-mercaptoethanol) 3.6 L, then a dissolving buffer 0.2 L, containing ammonium sulfate 150 g was added thereto. The solution was adjusted to pH 7.2 with aqueous ammonia and cooled to 4° C. A dissolving buffer 1.6 L containing PEG 6000, 540 g was added slowly thereto, and the mixture was stirred at 4° C. for 1 h. The precipitate (insoluble materials) was removed by centrifuging and the solution was added slowly to a dissolving buffer, 5.4 L containing PEG 6000, 650 g. The solution was warmed to 32° C. and a solution of 4M NaCl 540 ml was added with stirring for 20 min. Stirring at 32° C. for 1 h gave rod crystals of L-methionine γ-lyase in the solution. Then, the crystals were aged with stirring at 4° C. for 20 h, and collected by centrifugal separation as crude crystals.

Example 4

Preparation of Crystals of L-Methionine γ-Lyase

The crude rod crystal obtained in Example 3 was dissolved in a dissolving buffer 6 L and the precipitate (insoluble materials) was removed by centrifuging. A dissolving buffer 2.4 L containing PEG 6000 760 g was added slowly and the mixture was warmed at 32° C. A solution of 4M NaCl 420 ml was added with stirring during 20 min. Octahedral crystals of L-methionine γ-lyase appeared after stirring at 32° C. for 1 h and 4° C. for 20 h. The crystals of L-methionine γ-lyase were collected by centrifuging and dissolved in a dissolving buffer 6 L. L-Methionine γ-lyase 125 g was there in the obtained solution for recrystallization 6.3 L and the specific activity was ca. 55 U/mg. The specific activity was measured according to the procedure by Esaki, et al., [Methods Enzymol., 143, 459–465 (1987)].

Example 5

Column Chromatography of L-Methionine γ-Lyase

A dissolved solution of the recrystallized material obtained in Example 4 was applied to column chromatography on DEAE-Sepharose FF (Amersham Pharmacia Biotech Co.) 5 L which was previously equilibrated in a 20 mM sodium phosphate buffer (pH 7.2). After the column was washed with a 20 mM sodium phosphate buffer (pH 7.2) containing 0.1 mM of PLP and 0.01% 2-mercaptoethanol, the product was eluted with a 20 mM sodium phosphate buffer (pH 7.2) containing 120 mM NaCl, 0.1 mM PLP and 0.01% 2-mercaptoethanol. The active fraction 15 L was concentrated by the use of a filtration membrane (Millipore Co.) of molecular weight cut off, 10 kDa to 2.7 L. L-Methionine γ-lyase 87 g was there in the concentrated solution. A portion of 0.9 L of the concentrated solution 2.7 L was applied to column chromatography on Sephacryl S-200HR (Amersham Pharmacia Biotech Co.) 18 L which was previously equilibrated in a 20 mM sodium phosphate buffer (pH 7.5) containing 0.01 mM PLP. The procedure repeated three times. The specific activity of obtained L-methionine γ-lyase of the active fraction was about 61 U/mg and L-methionine γ-lyase 69 g was there.

The specific activity and the yield of L-methionine γ-lyase at each treatment of examples 3 to 5 are shown in Table 1.

TABLE 1

| | Purification step | specific activity (U/mg) | Activity yield (%) |
|---|---|---|---|
| Example 2 | Crude enzyme soln. | 28.7 | 100 |
| Example 3 | Rod crystal | 54.5 | 88 |
| Example 4 | Octagonal crystal Soln. | 55.4 | 82 |
| Example 5 | Sephacryl S-200 HR | 61.2 | 50 |

Example 6

Preparation of Crystals of L-Methionine γ-Lyase

A recrystallization for an X-ray diffraction experiment was carried out by the use of the solution (sample solution) obtained in Example 5. The vapor-diffusion method (Sitting Drop method) was used as the method of recrystallization (FIG. 1). First of all, two kinds of solutions were prepared for the recrystallization. A solution for crystallization 1 (containing a 50 mM sodium phosphate buffer, pH 7.2; 1% ammonium sulfate, 40% 2-methyl-2,4-penatnediol) and a solution for crystallization 2 (containing a 50 mM sodium phosphate buffer, pH 7.2; 1% ammonium sulfate and PEG 6000) were prepared. The solution for crystallization 1 500 µl and the solution for crystallization 2 100 µl were mixed and used as an outer solution.

Then, 10 µl of the outer solution was taken out and mixed with 10 µl of sample solution, which was filtrated with a membrane filter. The mixed solution was used as an inner solution. The plates for the crystallization was immediately set in a chamber adjusted at 4° C. Tiny crystals were appeared after 2 days and it was recognized through the microscopic observation. The crystal grew up to 0.5×0.5× 0.3 mm after 1 week standing.

Example 7

Structure Analysis of a Crystal of L-Methionine γ-Lyase

An X-ray crystallographic analysis of L-methionine γ-lyase was carried out on the crystal obtained in Example 6. The intensity of the diffraction of the crystal was measured by means of an imaging plate X-ray diffracting device (R-AXIS IV) of Rigaku Co. at the synchrotron Facility (Spring-8) according to a procedure cited in Table 2. The obtained diffraction images were treated with software, DENZO (HKL Research Co.). The analysis results are shown in Tables 3 and 4.

TABLE 2

| Measurement conditions | |
|---|---|
| Size of Cryst. | 0.5 × 0.5 × 0.3 mm |
| wave length of X-RAY | 0.835 Å |
| Camera radius | 320 mm |
| Size of collimator | 0.1 mm |
| exposure time of X-RAY | 8 min |
| Region of vibration angle | 0.8 degree |

TABLE 3

Shell I/Sigma in resolution shells:

| Lower limit | Upper limit | % of reflections with I/Sigma less than | | | | | | | | |
|---|---|---|---|---|---|---|---|---|---|---|
| | | 0 | 1 | 2 | 3 | 5 | 10 | 20 | >20 | total |
| 40.00 | 3.88 | 0.8 | 1.4 | 1.8 | 2.1 | 2.8 | 4.9 | 18.2 | 81.4 | 99.6 |
| 3.88 | 3.08 | 0.9 | 1.5 | 2.2 | 3.0 | 5.0 | 14.0 | 62.6 | 36.5 | 99.1 |
| 2.69 | 2.44 | 2.1 | 4.7 | 7.6 | 11.1 | 18.0 | 44.3 | 95.5 | 4.1 | 99.7 |
| 2.44 | 2.27 | 3.0 | 7.0 | 12.3 | 17.6 | 27.6 | 57.4 | 98.9 | 0.9 | 99.7 |
| 2.27 | 2.13 | 3.8 | 9.6 | 17.0 | 23.8 | 36.6 | 68.7 | 99.8 | 0.1 | 99.9 |
| 2.13 | 2.03 | 5.6 | 13.9 | 23.6 | 32.8 | 48.3 | 77.4 | 99.6 | 0.4 | 100.0 |
| 2.03 | 1.94 | 7.5 | 19.8 | 33.4 | 44.8 | 61.0 | 85.0 | 99.6 | 0.4 | 100.0 |
| 1.94 | 1.86 | 10.9 | 28.6 | 46.1 | 58.9 | 75.2 | 94.0 | 99.4 | 0.0 | 99.5 |
| 1.86 | 1.80 | 15.2 | 37.6 | 57.0 | 68.4 | 80.5 | 90.3 | 92.0 | 0.0 | 92.1 |
| All | hkl | 5.1 | 12.6 | 20.4 | 26.7 | 36.3 | 56.4 | 85.0 | 13.9 | 98.9 |

TABLE 4

| Shell limit | Angstrom | | Average I | Average | | Norm Chi**2 | Linear R-fac | Square R-fac |
|---|---|---|---|---|---|---|---|---|
| | Lower | Upper | | error | stat. | | | |
| | 40.00 | 3.88 | 5214.9 | 199.5 | 86.1 | 1.043 | 0.059 | 0.072 |
| | 3.88 | 3.08 | 3402.8 | 206.4 | 73.8 | 0.977 | 0.084 | 0.094 |
| | 3.08 | 2.69 | 1455.5 | 112.0 | 46.7 | 0.980 | 0.116 | 0.122 |
| | 2.69 | 2.44 | 871.2 | 74.5 | 39.2 | 1.077 | 0.153 | 0.152 |
| | 2.44 | 2.27 | 619.7 | 61.3 | 38.7 | 1.121 | 0.199 | 0.191 |
| | 2.27 | 2.13 | 508.4 | 59.4 | 42.2 | 1.114 | 0.246 | 0.230 |
| | 2.13 | 2.03 | 375.0 | 53.5 | 44.6 | 1.118 | 0.315 | 0.288 |
| | 2.03 | 1.94 | 250.3 | 48.1 | 45.0 | 1.055 | 0.428 | 0.386 |
| | 1.94 | 1.86 | 165.4 | 50.0 | 48.0 | 0.936 | 0.552 | 0.484 |
| | 1.86 | 1.80 | 110.1 | 57.3 | 57.0 | 0.888 | 0.723 | 0.611 |
| All reflections | | | 1330.6 | 93.2 | 52.3 | 1.041 | 0.110 | 0.088 |

Summary of reflections intensities and R-factors by shells
R linear = SUM (ABS(I − <I>)) / SUM (I)
R square = SUM ((I − <I>)  2) / SUM (I  2)
Chi2 = SUM ((I − <I>)  2) / (Error ** 2 * N / (N − 1)))
In all sums single measurements are excluded The crystal structure was solved by means of molecular replacement method the program package X-PLOR [A. T. Brunger, X-PLOR, Version 98.0: Yale University Press: New Haven, Conn., 1998; Molecular Simulations, Inc.]. The used molecular structure model is Cystathionine β-Lyase (PDB ID=1CL1). Refinement of the structure gave the R-value 0.234 (R free=0.2919) for the 153779 reflections of more than 2 σ. In the refinement, 721 water molecules are obtained by the electron density map and included in the structural calculation.

Example 8

Construction of Functionally Modified L-Methionine γ-Lyase Gene

Functionally modified L-methionine γ-lyase gene was constructed by the use of Quick Change Site-Directed Mutagenesis Kit (StrataGene Co.) to obtain functionally modified L-methionine γ-lyase, wherein Lys-6 is substituted by His, Cys-49 is substituted by Ser, Ala-119 is substituted by Ser, Phe-128 is substituted by Cys, Cys-190 is substituted by Ser, Gly-217 is substituted by Ser, Ser-248 is substituted by Cys, Leu-341 is substituted by His, Asp-385 is substituted by Cys, Lys-395 is substituted by His and Gly-9 is substituted by Cys and Asp-385 is substituted by Cys in the amino acid sequence described in SEQ ID NO: 1 (hereafter each enzyme is shown to be K6H (SEQ ID NO:3), C49S (SEQ ID NO:24), A119S (SEQ ID NO:12), F128C (SEQ ID NO:9), C190S (SEQ ID NO:25), G217S (SEQ ID NO:26), S248C (SEQ ID NO:10), L341H (SEQ ID NO:14), D385C, K395H (SEQ ID NO:6) and G9C+D385C (SEQ ID NO:2) and wild type L-methionine γ-lyase is shown to be WT (SEQ ID NO:1)). A synthetic oligonucleotide primer in which a site specific mutation was inserted was prepared and the mutation was introduced according to the procedure of the protocol. Two types of the synthetic oligonucleotide primers with forward and inverse directions were prepared. The oligonucleotide primers with forward direction are shown in Table 5 (SEQ ID NOS:15–23).

An annealing of the transducing primer of a mutation was carried out in the concerned region of the plasmid and modified plasmid DNA was prepared by means of a Pfu Turbo DNA polymerase (StrataGene Co.). After the reaction was repeated 16 times, template DNA was digested with a restriction enzyme DpnI. Then, an E. coli, JM109 strain was transformed. The viable transformant was cultivated in the LB medium and the plasmid was extracted. The DNA sequence was confirmed by means of a dideoxy termination method. The nucleic acid sequences are shown in the Sequence listing, SEQ ID NO:15 to SEQ ID NO:23.

TABLE 5

| | |
|---|---|
| K6H | 5'-CTATATGCACGGCTCCAACCATCTCCCAGGATTTGCCAC-3'<br>(SEQ ID NO:15) |
| C49S | 5'-GAATACGGCGCTGCGAGCTTTGCCGGCGAG-3'<br>(SEQ ID NO:16) |
| F128C | 5'-GGCATCGGCGAGTGCGGGGTCAAGCTG-3'<br>(SEQ ID NO:17) |
| C190S | 5'-GTCGACAACACCTACAGCACGCCGTACCTG-3'<br>(SEQ ID NO:18) |
| G217S | 5'-CCTGAGCGGCCATAGCGACATCACTGC-3'<br>(SEQ ID NO:19) |
| S248C | 5'-CGGTGCGGTGCTCTGCCCCCATGACGCCG-3'<br>(SEQ ID NO:20) |
| L341H | 5'-CGCGCGGTGAGCCATGGCGATGCCGAG-3'<br>(SEQ ID NO:21) |
| D385C | 5'-CTGGAAGACATCGACTGCCTGCTGGCCGATGTG-3'<br>(SEQ ID NO:22) |
| G9C | 5'-CCAACAAGCTCCCATGCTTTGCCACCCGCG-3'<br>(SEQ ID NO:23) |

Example 9

Preparation of Functionally Modified L-Methionine γ-Lyase

The transformed strain obtained in Example 8 was cultivated in 10 tubes of the 10 ml LB medium containing 0.5% glycerin and then cultivated in a Terrific medium 120 ml containing 4% glycerin at 28° C. for 24 h. Isopropyl-β-dithiogaractopyranoside was added so as to be a 0.3 mM solution of the final concentration at the logarithmic growth phase to induce the expression of L-methionine γ-lyase. After cultivation, the cells were harvested by centrifuging, suspended in a 100 mM phosphate buffer 40 ml containing 1 mM EDTEA-2Na, 0.75 mM PLP and 0.01% DTT and then disrupted by means of a high pressure homogenizer. Filter aid, Coporoc-SA (Otsuka Pharmaceuticals Co.) was added so as to be a 0.6% solution (w/w) in the final concentration and the impurity was removed by centrifuging. Ammonium sulfate was added so as to be a 60% saturated solution in the final concentration at 5° C. with keeping pH 7.2. The salt-outed product was collected by centrifuging and dissolved in a 20 mM sodium phosphate buffer (pH 7.2) 25 ml containing 0.5 mM PLP and 0.05% 2-mercaptoethanol. PEG 6000 was added so as to be an 8% solution in the final concentration and the impurity was removed by centrifuging. Then, NaCl was added so as to be 200 mM in the final concentration at 37° C. After maintaining at 5° C. overnight, the appeared crystals were collected by centrifuging and dissolved in a 20 mM sodium phosphate buffer (pH 7.2) containing 0.5 mM PLP and 0.05% 2-mercaptoethanol. The solution showed a single band in an electrophoresis on SDS polyacrylamide gel and showed to be pure and yield enough for the examination on the property analysis of functionally modified L-methionine γ-lyase.

Example 10

Property of Functionally Modified (Acquirement of High Activity Mutant)

The specific activity of purified functionally modified L-methionine γ-lyase obtained in Example 9 is shown in Table 6, comparing with that of wild type L-methionine γ-lyase as 100. The activity was measured according to the procedure by Soda et al. [Methods Enzymol., 143, 459–465 (1987)], wherein the production rate of α-ketobutyrate acid was measured in the presence of L-methionine,

TABLE 6

| Functionally modified enzyme | Specific activity (%) |
|---|---|
| K6H | 122 |
| F128C | 112 |
| C190S | 120 |
| S248C | 131 |
| D385C | 102 |
| WT | 100 |

Every functionally modified enzyme obtained showed an increase of specific activity than that of wild type L-methionine γ-lyase.

Example 11

Property of Functionally Modified L-Methionine γ-Lyase (pH Stability)

The purified functionally modified L-methionine γ-lyase obtained in Example 9 was incubated in a 0.1 M sodium carbonate buffer (pH 11.0) at 37° C. for 3 h and the remaining activity was measured. The comparative remaining activity was shown in Table 7, in comparison with the remaining activity value 100 in a 0.1 M sodium phosphate buffer (pH 8.0). The activity was measured according to the procedure by Soda et al. [Methods Enzymol., 143, 459–465 (1987)], wherein the production rate of α-ketobutyrate was measured in the presence of L-methionine.

The remaining activity of C49S showed that the tolerance against alkaline pH increased in comparison with that of the wild type L-methionine γ-lyase.

TABLE 7

| Functionally modified enzyme | Remaining activity (%) |
|---|---|
| C49S | 87 |
| WT | 79 |

Example 12

Property of Functionally Modified L-Methionine γ-Lyase (Thermal Stability)

The purified functionally modified L-methionine γ-lyase obtained in Example 9 was incubated in a 0.1 M sodium phosphate buffer (pH 7.2) at 65° C. for 30 min and the remaining activity was measured. The comparative remaining activity was shown in Table 8, in comparison with the remaining activity 100 at 37° C. The activity was measured according to the procedure by Soda et al. [Methods Enzymol., 143, 459–465 (1987)], wherein the production rate of α-ketobutyrate was measured in the presence of L-methionine.

The thermal stability of G9C+D385C increased drastically in comparison with that of wild type of L-methionine γ-lyase.

TABLE 8

| Functionally modified enzyme | Remaining activity (%) |
|---|---|
| G9C + D385C_ | 80 |
| WT | 10 |

Example 13

Property of Functionally Modified L-Methionine γ-Lyase (Affinity to PLP)

The purified functionally modified L-methionine γ-lyase obtained in Example 9 was once dialyzed in a 0.1 M sodium phosphate buffer (pH 7.2) and excess PLP was removed and the activity value in the presence of PLP was compared with that in the absence of PLP. The comparative remaining activity was shown in Table 9, in comparison with the remaining activity value 100 with that with PLP. The activity was measured according to the procedure by Soda et al. [Methods Enzymol., 143, 459–465 (1987)], wherein the production rate of α-ketobutyrate was measured under in the presence of L-methionine.

TABLE 9

| Functionally modified enzyme | Activity without PLP (%) |
|---|---|
| C19OS | 81 |
| L341H | 80 |
| WT | 75 |

Since the dissociation of PLP was protected, the activity value of every functionally modified enzyme increased in comparison with that of the wild type of L-methionine γ-lyase.

Example 14

Property of Functionally Modified L-Methionine γ-Lyase (Substrate Specificity)

The substrate specificity of the purified functionally modified L-methionine γ-lyase obtained in Example 9 was investigated. The activity was measured according to the procedure by Soda et al. [Methods Enzymol., 143, 459–465 (1987)], wherein the production rate of α-ketobutyrate was measured in the presence of 250 mM L-homoserine and 25 mM L-methionine as the substrate and their values were compared. The comparative specific activity was shown in Table 10, wherein the case of L-methionine against that of L-homoserine was taken to be 100 in wild type of L-methionine γ-lyase.

TABLE 10

| Functionally modified enzyme | Activity (%) |
|---|---|
| G217S | 188 |
| S248C | 127 |
| WT | 100 |

The activity against L-methionine increased in every functionally modified enzyme. Furthermore, Km value to L-methionine of S248D and wild type of L-methionine γ-lyase was obtained. The Km value of wild type L-methionine γ-lyase was 1.3 mM and that of S248C was 1.0 mM. An affinity to L-methionine increased in S248C enzyme.

Example 15

Property of Functionally Modified L-Methionine γ-Lyase (Substrate Specificity)

The substrate specificity of the purified functionally modified L-methionine γ-lyase obtained in Example 9 was investigated. The activity was measured according to the procedure by Soda et al. [Methods Enzymol., 143, 459–465 (1987)], wherein the production rate of α-ketobutyrate was measured in the presence of 12.5 mM D,L-homocysteine and 25 mM L-methionine as the substrate and their values were compared. The comparative specific activity was shown in Table 11, wherein the case of L-methionine against that of D,L-homoserine was taken to be 100 in wild type of L-methionine Y-lyase.

The activity against L-methionine increased in every functionally modified enzyme.

TABLE 11

| Functionally modified enzyme | Activity (%) |
|---|---|
| K6H | 165 |
| F128C | 136 |
| S248C | 178 |
| WT | 100 |

INDUSTRIAL APPLICABILITY

A functionally modified recombinant L-methionine γ-lyase of the present invention is obtained by cultivation of a recombinant E-coli in a suitable medium, and constitutes naturally an active form which comprises a tetramer in the soluble fraction (cell-free extracts). The protein or the polymer of its mutant of the present invention, or preferably an enzyme of the tetramer is useful as a therapeutic agent for tumor, obesity, heart disease, cardiovascular disease, CNS, aging and the like.

The invention claimed is:

1. A functionally modified protein having the amino acid sequence according to SEQ ID NO: 1 except for one or more substitution mutations selected from group consisting of: Lys6 to His, Gly-9 to Cys, Cys-49 to Ser, Cys-116 to Ser or Tyr, Ala-119 to Ser, Phe-128 to Cys, Cys-190 to Ser, Gly-217 to Ser, Ser-248 to Cys, Leu341 to His, Asp-382 to Pro and/or Asp-385 to Cys.

2. The protein as claimed in claim 1, wherein its tetramer structure of L-methionine γ-lyase is stabilized.

3. The protein as claimed in claim 1, wherein its dimer structure of a subunit of L-methionine γ-lyase is stabilized.

4. The protein as claimed in claim 3, wherein Cys-116 is substituted by Ser or Tyr, Ala-119 is substituted by Ser, Phe-128 is substituted by Cys and/or Ser-248 is substituted by Cys, in the amino acid sequence described in SEQ ID NO: 1.

5. The protein as claimed in claim 1, wherein said mutation prevents a dissociation of pyridoxal 5'-phosphate, a coenzyme of L-methionine γ-lyase.

6. The protein as claimed in claim 5, wherein Cys-190 is substituted by Ser and/or Leu-341 is substituted by His, in the amino acid sequence described in SEQ ID NO: 1.

7. The functionally modified protein according to claim 1, wherein said one or more mutations stabilize the association of dimers, stabilize the dimer structure of a subunit and prevent dissociation of the co-enzyme, pyridoxal 5'-phosphate.

8. The protein as claimed in claim 1, wherein said substitution mutation is selected from the group consisting of: Lys-6 is substituted by His, Gly-9 is substituted by Cys, Cys-116 is substituted by Ser or Tyr, Phe-128 is substituted by Cys, Ser-248 is substituted by Cys, Leu-341 is substituted by His, Asp-382 is substituted by Cys and/or Lys-395 is substituted by His and wherein said substitution mutation stabilizes the association between dimers and the dimeric structure of the protein and prevents the dissociation of the coenzyme, pyridoxal 5'-phosphate from the protein.

9. The protein as claimed in claim 1, wherein the mutation increases the lyase activity of the protein in comparison with the lyase activity of wild type L-methionine γ-lyase.

10. The protein as claimed in claim 9, having a mutation, wherein Lys-6 is substituted by His, Phe-128 is substituted by Cys, Cys-190 is substituted by Ser, Ser-248 is substituted by Cys and/or Asp-385 is substituted by Cys, in the amino acid sequence described in SEQ ID NO: 1.

11. The protein as claimed in claim 1, wherein the mutation stabilizes the protein in an alkaline solution.

12. The protein as claimed in claim 1, wherein the mutation stabilizes the protein at high temperature.

13. The protein as claimed in claim 1, wherein the mutation increases the substrate specificity of the enzyme.

14. The protein as claimed in claim 13, having a mutation, wherein Gly-217 and Ser-248 are substituted by Cys in the amino acid sequence described in SEQ ID NO: 1.

* * * * *